United States Patent [19]

Toepfer et al.

[11] Patent Number: 6,136,790
[45] Date of Patent: Oct. 24, 2000

[54] CARBOHYDRATE MIMETICS HAVING ANTIADHESIVE PROPERTIES

[75] Inventors: Alexander Toepfer, Kriftel; Gerhard Kretzschmar, Eschborn; Eckart Bartnik, Wiesbaden; Dirk Seiffge, Mainz-Kostheim, all of Germany

[73] Assignee: Glycorex AB, Sweden

[21] Appl. No.: 08/999,957

[22] Filed: Jul. 28, 1997

Related U.S. Application Data

[63] Continuation of application No. 08/403,526, Mar. 13, 1995, abandoned.

[30] Foreign Application Priority Data

Mar. 11, 1994 [DE] Germany .............................. 44 08 248

[51] Int. Cl.$^7$ ............................ A61K 31/70; C07H 15/00
[52] U.S. Cl. ................................ 514/25; 514/23; 514/54; 514/61; 514/62; 536/4.1; 536/17.2; 536/17.5; 536/18.5; 536/18.6; 536/18.7; 536/33; 536/53; 536/54; 536/55; 536/55.1; 536/55.2; 536/55.3; 536/118; 536/124
[58] Field of Search ................................. 514/23, 25, 54, 514/61, 62; 536/4.1, 17.2, 17.5, 18.5, 18.6, 18.7, 33, 53, 54, 55, 55.1, 55.2, 55.3, 118, 124

[56] References Cited

U.S. PATENT DOCUMENTS

| | | | |
|---|---|---|---|
| 5,079,353 | 1/1992 | Ratcliffe et al. | 536/53 |
| 5,162,513 | 11/1992 | Wong | 536/1.1 |

FOREIGN PATENT DOCUMENTS

| | | |
|---|---|---|
| 0 579 196 A1 | of 1993 | European Pat. Off. |
| 0 627 442 A1 | of 1993 | European Pat. Off. |
| 6-306092 | 11/1994 | Japan . |
| WO 91/19501 | of 1991 | WIPO . |
| WO 92/00245 | 1/1992 | WIPO . |
| WO 92/00251 | 1/1992 | WIPO . |
| WO 92/09870 | 6/1992 | WIPO . |
| WO 92/16640 | 10/1992 | WIPO . |
| WO 92/18610 | 10/1992 | WIPO . |
| 0 536 394 | 4/1993 | WIPO . |

OTHER PUBLICATIONS

Green et al. (*Biochem. Biophys. Res. Commun.* Oct. 15, 1992, 188(1), 244–251).
Needham et al. (*Proc. Nat. Acad. Sci. USA* Feb. 1993, 90, 1359–1363).
Mulligan et al., "Protective Effects of Oligosaccharides in P–Selectin–Dependent Lung Injury," *Nature*, 364: 149–151 (1993).
Toepfer et al., Synthesis of Novel Mimetics of the Sialyl Lewis X Determinant, *Tetrahedron Letters*, 36:9161–64 (1995).
Horie et al., "Preparation of Monosaccharide or Oligosaccharide Derivatives Containing' Fucose and/or (di)Glutamic Acid or Lysine with Specific Binding Affinity to Adhesion Molecule ELAM–1," *Chemical Abstracts*, 123(13): Abs. No. 170190 (1995).

Ravindranath et al., "An Epitope Common to Gangliosides O–Acetyl–$G_{D3}$ and $G_{D3}$ Recognized by Antibodies . . . ", *Cancer Research*, 49:3891–3897 (1989).
Eckelman, Ed., "In Vivo Diagnosis and Therapy of Human Tumors with Monoclonal Antibodies", Proceedings of a Symposium held in Naples, Italy, Mar. 16–19, 107–185 (1988).
Houghton et al., "Monoclonal Antibodies: Potential Applications to the Treatment of Cancer", *Seminars in Oncology*, 13:165–179 (1986).
Foster et al., "Production of TNFα by LPS–stimulated murine, rat and human blood and its pharmacological modulation", *Agents Actions*, 38:C77–C79 (1993).
Lowe et al., "ELAM–1–Dependent Cell Adhesion to Vascular Endothelium Determined by a Transfected Human Fucosyltransferase cDNA", *Cell*, 63:475–484 (1990).
Reutter et al., "Biological Significance of Sialic Acids", *10 Cell Biology Monographs*, 263–305 (1982).
Menger et al., "Scope and perspectives of intravital microscopy–bridge over from in vitro to in vivo", *Immunology Today*, 14:519–522 (1993).
Atherton et al., "Measurement of Granulocyte Adhesiveness", *J. Physiol.*, 222:447–474 (1972).
Springer, "Traffic Signals for Lymphocyte Recirculation and Leukocyte Emigration: The Multistep Paradigm", *Cell*, 76:301–314 (1994).
Springer, "Adhesion receptors of the immune system", *Nature*, 346:425–434 (1990).
Harlan, "Leukocyte–Endothelial Interactions", *Blood*, 65:513–525 (1985).
Schmidt, "Neue Methoden zur Glyosid– und Oligosaccharidsynthese—gibt es Alternativen zur Koenigs–Knorr–Methode?", *Angew. Chem.*, 98:213–236 (1986).
Kuhn et al., "Synthese anomerer Sialinsäure–methylketoside", *Chem. Ber*, 9:611–617 (1966).

*Primary Examiner*—Kathleen K. Fonda
*Attorney, Agent, or Firm*—Foley & Lardner

[57] ABSTRACT

The invention relates to carbohydrate mimetics, which inhibit the binding of selectin to carbohydrate ligands, of the formula I

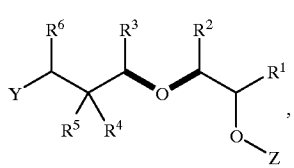

excluding the compounds sialyl-Lewis-X and -A and their derivatives which, instead of an N-acetyl group, carry the substituents $N_3$, $NH_2$ or OH or which, instead of fucose, carry glycerol,
and pharmaceutical compositions and diagnostic agents containing these derivatives, and methods for using these pharmaceutical compositions and diagnostic agents.

38 Claims, No Drawings

CARBOHYDRATE MIMETICS HAVING ANTIADHESIVE PROPERTIES

This application is a continuation of application Ser. No. 08/403,526, filed Mar. 13, 1995, now abandoned.

BACKGROUND OF THE INVENTION

The present invention relates to carbohydrate mimetics that inhibit cell adhesion involved in several pathological responses, and methods of producing such derivatives. The invention further relates to pharmaceutical compositions and diagnostic agents containing these derivatives, and methods using these pharmaceutical compositions and diagnostic agents.

Endothelial cells and various circulating cells of the hematolymphoid system express unique surface glycoproteins known as selecting, which mediate intercellular adhesion. (K.-A. Karlsson, *TIPS* 12: 265–272 (1991)). Intercellular adhesion plays an important role in many pathological responses. For example, the adherence of platelets and leukocytes to vascular surfaces is a critical component of the inflammatory response and is part of a complex series of reactions involving the simultaneous and interrelated activation of the complement, coagulation and immune systems. In addition, leukocyte adherence to vascular endothelium is a key initial step in the migration of leukocytes to tissues in response to microbial invasion.

Compounds that block this initial adhesive interaction are thus expected to have efficacy in the treatment of inflammatory diseases such as rheumatoid arthritis, asthma, and psoriasis. Other indications include adult respiratory distress syndrome, reperfusion injury, ischemia, ulcerative colitis, vasculitis, atherosclerosis, and inflammatory bowel disease. (Boschelli et al., U.S. Pat. No. 5,356,926). Synthetic analogs (mimetics) of carbohydrate ligands that bind specifically to selectins, and thus inhibit selectin-mediated intercellular adhesion, have been implicated as promising therapeutics as anti-inflammatories and anti-coagulants (T. A. Springer, L. A. Lasky, *Nature* 349: 196–197 (1991); T. Feizi, *TIBS* 16: 84–86 (1991)).

In addition, carbohydrate ligands are involved in bacterial and viral infections and cancer. Carbohydrate ligands are recognition domains for viruses (J. C. Paulson, *The Receptors*, Vol. II, P. M. Conn, ed., Academic Press, 131 (1985)), bacteria (Strömberg et al., *EMBO J.* 9: 2001 (1990)) and toxins (Karlsson et al., *Sourcebook of Bacterial Protein Toxins*, eds. J. E. Alouf, J. H. Freer, Academic Press, 56: 3537 (1990)). Carbohydrate mimetics are thus expected to have efficacy in the prevention and treatment of bacterial and viral infections and sepsis.

Cancer cells express carbohydrate ligands in patterns different from those in normal cells. Carbohydrate mimetics could be used to generate antibodies that recognize the naturally occurring carbohydrate ligands and thus facilitate the diagnosis of cancer. Because leukocyte adherence to vascular endothelium is also relevant to tumor cell metastasis, synthetic analogs that inhibit selectin-mediated intercellular adhesion are expected to have efficacy in the treatment of metastatic conditions. (S.-i. Hakomori, *Cancer Cells*, Vol. 3, No. 12 (December 1991)).

With regard to selectin-mediated intercellular adhesion, silylated and fucosylated carbohydrate ligands, specifically sialyl-Lewis-X[αNeu5Ac(2→3)βGal(1→4)[αFuc(1→3)]-βGlcNAc-OR] and sialyl-Lewis-A [αNeu5Ac(2→3)βGal (1→3)[αFuc(1→4)]-βGlcNAc-OR] (where R is defined as an aglycone having at least one carbon atom), are particularly important. (Schauer, ed., "Sialic Acids" in *Cell Biology Monographs*, Vol. 10 (1982); Lowe et al., *Cell*, 63: 475–485 (1990)). Both chemical (Ratcliff et al., U.S. Pat. No. 5,079,353) and chemical/enzymatic (A. Venot et al., PCT/CA 92/00251) syntheses of these compounds have been developed. These processes, however, are highly complex.

Therefore, research is presently underway to develop analogs that are easier to synthesize, but have equal or greater selectin binding affinity, than the naturally occurring carbohydrate ligands. Toward this end, several analogs, containing particular residue substitutions, have been synthesized. For example, neuraminic acid was replaced by lactic or glycolic acid, fucose was replaced by glycerol or trifluoromethylfucose, and N-acetylglycosamine was replaced by glycosamine or glucose (PCT/US 92/09870). Substitution of neuraminic acid by sulfate or phosphate has likewise been described (PCT/CA 92/00245). In addition, the replacement of glucosamine with a chain of at least 2 carbon atoms has been described (WO 92/18610). These efforts, however, have not elucidated whether oligo- or polyvalent structures can be synthesized from these substituted compounds. Furthermore, no methods have been described for the synthesis of compounds that contain a diol or similar group instead of the anomeric sugar.

To date, an efficient, enzymatic large-scale synthesis has been developed only for native sialyl-Lewis-X and sialyl-Lewis-A having slight modifications (C. H. Wong et al., WO 92/16640 and U.S. Pat. No. 5,162,513). These analogs, however, have the disadvantages of both a low affinity for corresponding selectins and a low in vivo stability (active substances are not orally available).

SUMMARY OF THE INVENTION

Accordingly, an object of the present invention is the economical and simple synthesis of carbohydrate mimetics that are stable physiologically and that have greater selectin binding affinity than their naturally occurring carbohydrate ligand counterparts. It is a further object of the present invention to use these carbohydrate mimetics to produce pharmaceutical compositions and diagnostic agents capable of diagnosing, preventing or treating bacterial or viral infections, tumor cell metastasis, and inflammatory pathologies.

These objectives are achieved by a compound of formula I

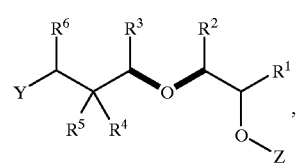

in which $R^1$ and $R^2$ independently of one another are H, $CH_2X$ or $CH_2O(CH_2)_m X^1$ or together form a six-membered carbo- or heterocycle having at least one substituent selected from the group consisting of $R^7$, $R^8$ and $R^9$ and $R^3$ is O, S, H or —$CH_2O$ $X^2$ and $R^4$ and $R^5$ independently of one another are O-α-N-acetylneuraminic acid (O-α-N-NANA), O-β-N-acetylneuraminic acid (O-β-N-NANA); $O(CR^{10}R^{11})_n COOH$, $OCX^3{}_2(CR^{10}R^{11})_n COOH$, $OSO_3H$ or another monobasic acid and $R^6$ is H, —OH or $C_1$–$C_{25}$-alkyl or, with $R^3$, forms a six-membered carbo- or heterocycle having at least one substituent $X^4$ and Y is O-β-N-acetylneuraminic acid (O-β-N-NANA), O-β-N-acetylneuraminic acid (O-β-N-NANA), $O(CR^{10}R^{11})_p$COOH, $OCX^3_2(CR^{10}R^{11})_p$COOH, $OSO_3H$ or another monobasic acid and Z is a pyranose, a furanose or an open-chain polyalcohol and m, n, p and q independently of one another are integers from 1 to 20 and $R^7$, $R^8$, $R^9$, X, $X^1$, $X^2$ and $X^4$ independently of one another are H, —$NH_2$, —COOH, —OH, —$CH_2OH$, —$CH_2NH$, $C_1$–$C_{25}$-alkyl, aryl or —$CH_2O(CH_2)_qX$ $X^3$ is H, $C_1$–$C_{25}$-alkyl or aryl or alternatively $X^3_2$ is =O or =S and $R^{10}$ and $R^{11}$ independently of one another are X or —$CH_2X$ or together form a six-membered carbo- or heterocycle having at least one substituent $X^4$, other than, i.e., the compounds sialyl-Lewis-X and -A and their derivatives which, instead of an N-acetyl group, carry the substituents $N_3$, $NH_2$ or OH or which, instead of fucose, carry glycerol.

The objectives set forth are further achieved by a method for producing a compound of formula I according to the invention, comprising the steps of (1) alkylating or glycosylating a functional group of an acceptor II

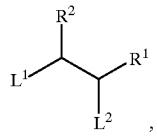

II containing at least two adjacent functional groups $L^1$ and $L^2$ and containing the substituents $R^1$ and $R^2$, with one equivalent of a donor III bearing at least two functional groups $L^3$ and $L^4$;

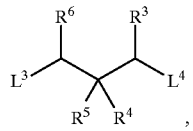

III one functional group $L^3$ of which is protected, if necessary, and the other functional group $L^4$ of which is optionally present in activated form, to achieve intermediate compound IV,

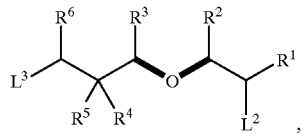

IV (2) alkylating, acylating or glycosylating the unprotected functional group $L^2$ of intermediate compound IV, with donor V having an activated functional group $L^5$

Z-$L^5$   V, the other functional groups which carry protective groups, if necessary, to achieve intermediate compound VI,

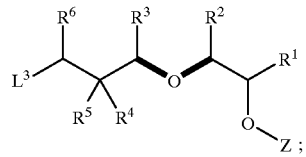

VI (3) selectively deprotecting and activating the functional group $L^3$ by reaction of intermediate compound VI with donor VII

Y-$L^6$   VII, which bears an activated functional group $L^6$ or protective groups, and (4) removing all protective groups to achieve a compound of formula I according to the invention, all variables having the meaning mentioned in the invention.

The objectives set forth are further achieved by pharmaceutical compositions prepared from compounds of formula I according to the invention, and the use of these pharmaceutical compositions in effective therapeutic amounts to prevent or treat bacterial or viral infections, tumor cell metastasis, and inflammation pathologies.

The objectives set forth are further achieved by pharmaceutical compositions for inhibiting the binding of a selectin to a carbohydrate ligand on a cell expressing a carbohydrate ligand, in which the composition comprises a compound of formula I of claim 1 in a pharmaceutically acceptable carrier.

The objectives set forth are further achieved by methods of inhibiting the binding of a selectin to a carbohydrate ligand on a cell expressing said carbohydrate ligand, in which a therapeutically effective dose of the pharmaceutical composition according to the invention is administered to a subject.

The objectives set forth are further achieved by an antibody against a compound of formula I and diagnostic kits for detecting a carbohydrate ligand that binds to a selectin.

The objectives set forth are further achieved by methods of detecting a selectin-expressing cell by contacting a sample suspected of containing said selectin-expressing cell with a compound of formula I according to the invention that is detectably labeled, and then detecting the binding of the selectin-expressing cell with the detectably labeled compound.

The objectives set forth are further achieved by methods of detecting in a sample a carbohydrate ligand by contacting a sample suspected of containing a carbohydrate ligand-expressing cell with a detectably labeled antibody according to the invention and then detecting the binding of the carbohydrate ligand-expressing cell with the detectably labeled antibody.

DETAILED DESCRIPTION OF PREFERRED EMBODIMENTS

Thus, the present invention relates to a compound that is a carbohydrate mimetic.

1. Preferably, the compound is the compound of formula I

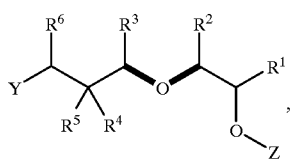

in which $R^1$ and $R^2$ independently of one another are H, $CH_2X$ or $CH_2O(CH_2)Mx^1$ or together form a six-membered carbo- or heterocycle having at least one of the substituents $R^7$, $R^8$ and $R^9$ and $R^3$ is O, S, H or —$CH_2OX^2$ and $R^4$ and $R^5$ independently of one another are O-α-N-acetylneuraminic acid (O-α-N-NANA), O-β-N-acetylneuraminic acid (O-β-N-NANA); $O(CR^{10}R^{11})_n COOH$, $OCX^3{}_2(CR^{10}R^{11})_n COOH$, $OSO_3H$ or another monobasic acid and $R^6$ is H, —OH or $C_1$–$C_{25}$-alkyl or, with $R^3$, forms a six-membered carbo- or heterocycle having at least one substituent $X^4$ and Y is O-α-N-acetylneuraminic acid (O-β-N-NANA), O-β-N-acetylneuraminic acid (O-β-N-NANA), $O(CR^{10}R^{11})_p COOH$, $OCX^3{}_2(CR^{10}R^{11})_p COOH$, $OSO_3H$ or another monobasic acid and Z is a pyranose, a furanose or an open-chain polyalcohol and m, n, p and q independently of one another are integers from 1 to 20 and $R^7$, $R^8$, $R^9$,

X, $X^1$, $X^2$ and $X^4$ independently of one another are H, —$NH_2$, —COOH, —OH, —$CH_2OH$, —$CH_2NH$, $C_1$–$C_{25}$-alkyl, aryl or —$CH_2O(CH_2)_q X$ $X_3$ is H, $C_1$–$C_{25}$-alkyl or aryl or alternatively $X^3{}_2$ is =O or =S and $R^{10}$ and $R^{11}$ independently of one another are X or —$CH_2{}^x$ or together form a six-membered carbo- or heterocycle having at least one substituent $X^4$, other than, i.e., the compounds sialyl-Lewis-X and -A and their derivatives which, instead of an N-acetyl group, carry the substituents $N_3$, $NH_2$ or OH or which, instead of fucose, carry glycerol, 2. in particular a compound of formula I which is distinguished in that $R^3$ and $R^6$ together form a β-D-galactosyl radical, 3. preferably wherein Z is an α-fucopyranosyl radical.

4. Preferred embodiments include a compound of formula I having the characterizing features of Nos. 2 and 3, which is distinguished in that Y is an O-α-N-acetylneuraminic acid radical and and $R^1$ and $R^2$ are H, namely (5a)

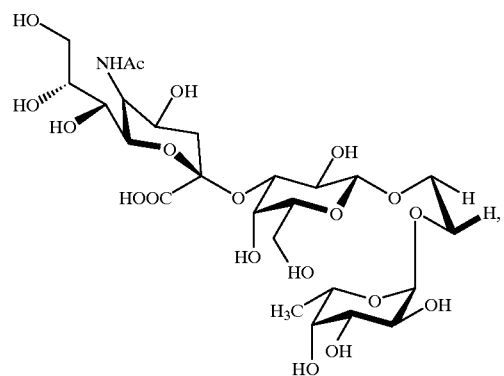

5. or which is distinguished in that

Y is an (O-α-N-acetylneuraminic acid radical and $R^1$ and $R^2$ are —$CH_2O(CH_2)_5 CH_3$, namely (5c)

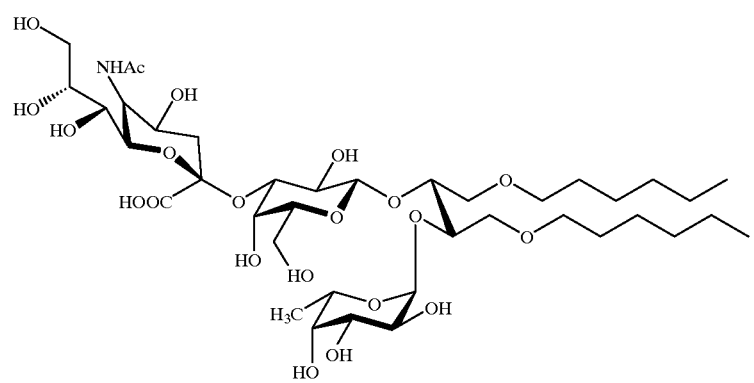

6. or preferably a compound of formula I having the characterizing features of Nos. 2 and 3, which is distinguished in that R$^1$ and R$^2$ together form a six-membered carbocycle and the substituents R$^7$, R$^8$ and R$^9$ are H, 7. in particular wherein Y is an O-α-N-acetylneuraminic acid radical, namely

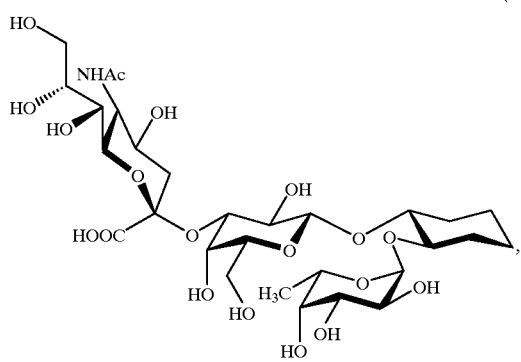
(5b)

8. or wherein

Y is HOOC—CH$_2$—O—, namely

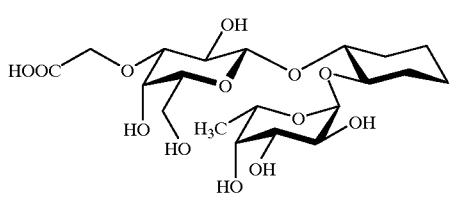
(7i)

9. or a compound having the features presented in No. 2, which is further distinguished in that R$^1$ and R$^2$ together form a six-membered carbocycle and the substituents R$^7$, R$^8$ and R$^9$ are H, Y is an O-α-N-acetylneuraminic acid radical and Z is an α-mannosyl radical, namely

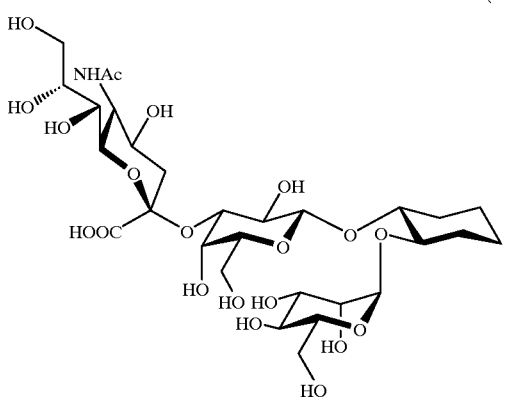
(7f)

10. or a compound having the features presented in No. 2, which is further distinguished in that R$^1$ and R$^2$ together form a six-membered carbocycle and the substituents R$^7$, R$^8$ and R$^9$ are H, Y is an O-α-N-acetylneuraminic acid radical and Z is an α-glucosyl radical, namely

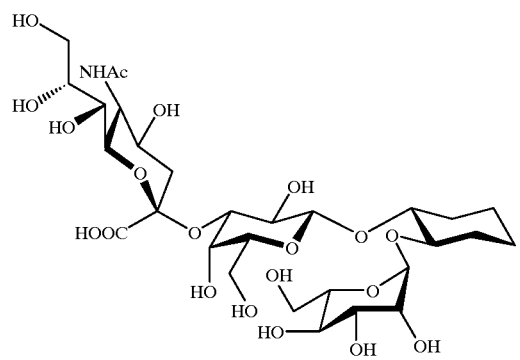
(7g)

11. or a compound having the features presented in No. 2, which is further distinguished in that R$^1$ and R$^2$ together form a six-membered carbocycle and the substituents R$^7$, R$^8$ and R$^9$ are H and Z is —CH$_2$C(CH$_2$OH)$_3$, 12. preferably wherein Y is an O-α-N-acetylneuraminic acid radical, namely

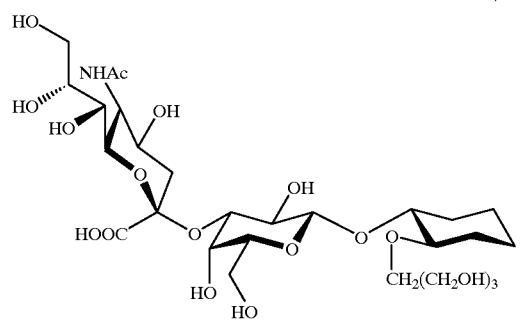
(22α)

13. or preferably wherein Y is an O-β-N-acetylneuraminic acid radical, namely

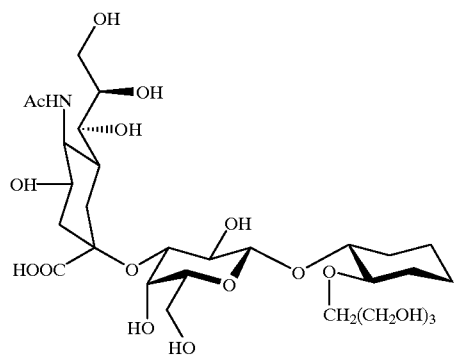
(22β)

14. or a compound having the features presented in No. 3, which is further distinguished in that R$^1$ and R$^2$ together form a six-membered carbocycle and the substituents R$^7$, R$^8$ and R$^9$ are H, Y is an O-α-N-acetylneuraminic acid radical and the β-D-galactosyl radical is substituted in the 2-O-position by a hexyl group, namely

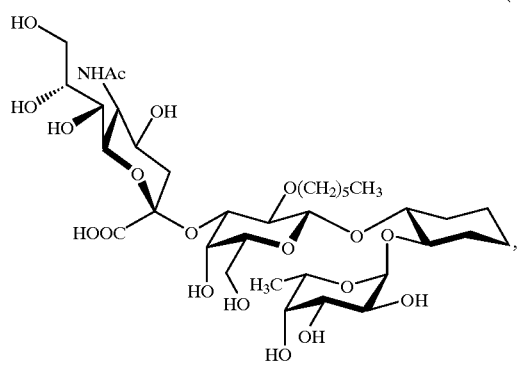

(23)

15. or a compound of formula I as in No. 1, which is distinguished in that
$R^1$ and $R^2$ together form a six-membered carbocycle,
$R^3$, $R^6$, $R^7$, $R^8$ and $R^9$ are H and
Z is an α-fucopyranosyl radical,
16. preferably wherein $R^4$ is H and $R^5$ is —OH,
17. in particular wherein Y is an O-α-N-acetylneuraminic acid radical, namely

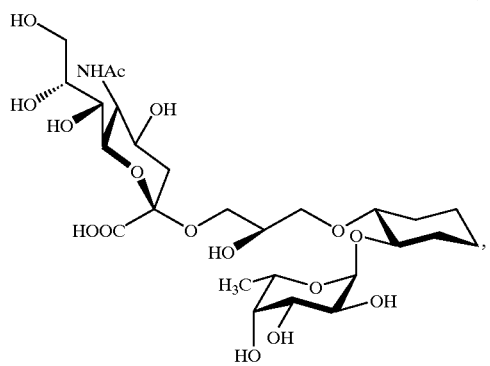

(18α)

18. or wherein Y is an O-β-N-acetylneuraminic acid radical, namely

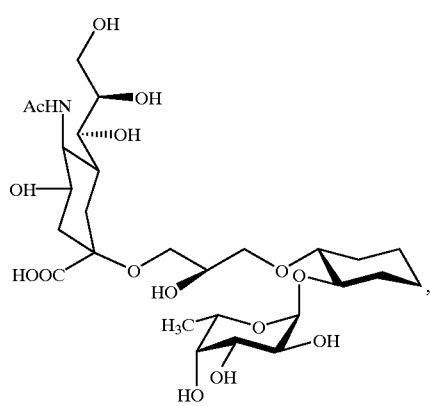

(18β)

19. or a compound having the features indicated in No. 15, which is distinguished in that $R^4$ and $R^5$ are H, 20. preferably wherein Y is an O-α-N-acetylneuraminic acid radical, namely

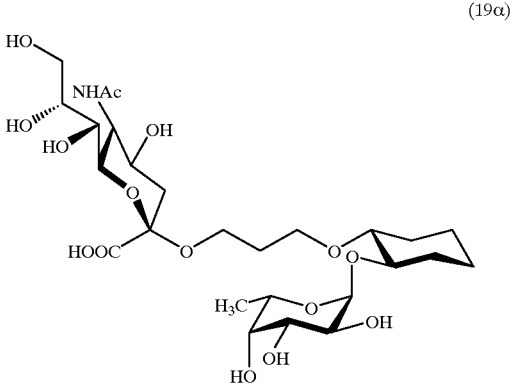

(19α)

21. or wherein Y is an O-β-N-acetylneuraminic acid radical, namely

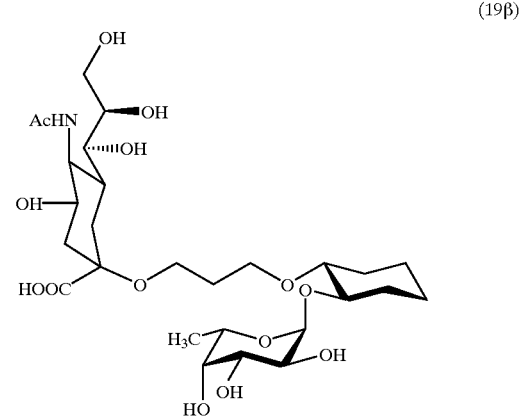

(19β)

22. or a compound having the features as in No. 15, which is distinguished in that $R^4$ and $R^5$ are —CH$_2$OH,
23. preferably wherein Y is an O-α-N-acetylneuraminic acid radical, namely

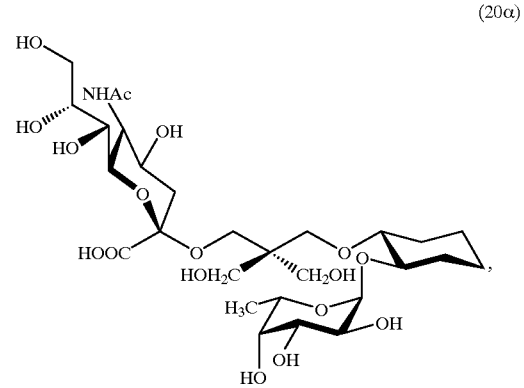

(20α)

24. or wherein Y is an O-β-N-acetylneuraminic acid radical, namely (20β)

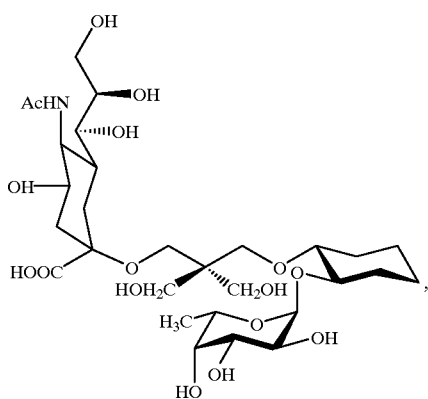

25. or a compound of formula I having the features as in No. 1, which is distinguished in that $R^1$ and $R^2$ together form a substituted tetrahydropyran ring and
$R^7$ and $R^8$ are H and
$R^9$ is —$CH_2O(CH_2)_qX$,
Z is an α-fucopyranosyl radical,
$R^3$ and $R^6$ together form a β-D-galactosyl radical and
Y is an O-α-N-acetylneuraminic acid radical,
26. preferably wherein
$R^9$ is —$CH_2O(CH_2)_5CH_3$, namely 27. or wherein $R^9$ is —$CH_2OH$, namely (24)

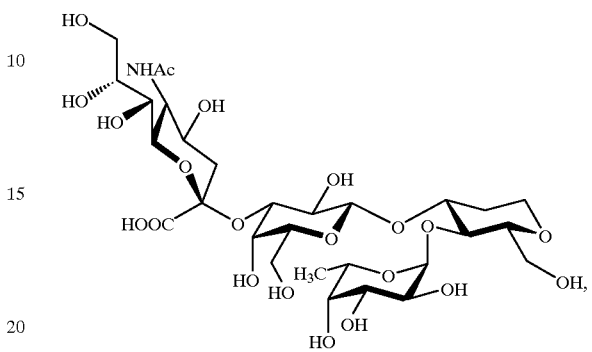

28. or wherein $R^9$ is —$CH_2O(CH_2)_3C_6H_5$, namely (7h)

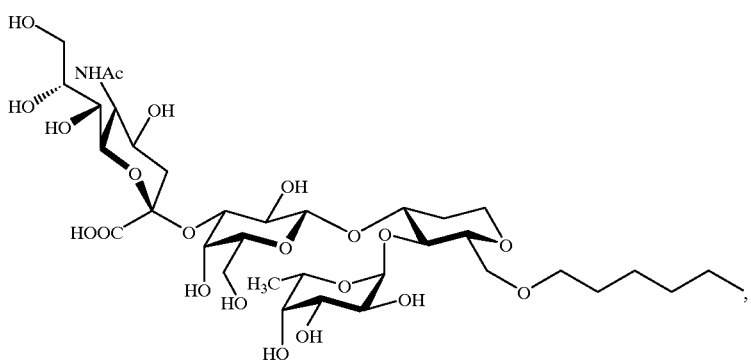

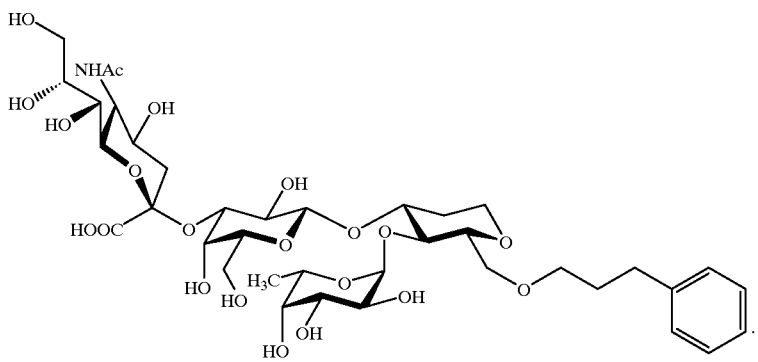

(7e)

A carbohydrate mimetic is a synthetic analog of an oligosaccharide, preferably sialyl-Lewis-X or -A, in which one or more sugars are replaced, one or more sugars are replaced by a chemical group or compound, preferably diols or polyols, that are not one of the sugars, and the α-configuration of a sugar occurring in the oligosaccharide is replaced by the β-configuration of the sugar, i.e., the stereochemistry at the anomeric center changes. These substitutions can result in a simplification of the compound's structure.

The carbohydrate mimetics according to the invention can be synthesized economically and simply to yield products that are highly stable physiologically and that have greater selectin binding affinity, e.g., for E- and/or P-selectin, than their naturally occurring carbohydrate ligand counterparts, e.g., sialyl-Lewis-X. If sugar components are replaced by simple alcohols, the synthesis cost is reduced considerably without affecting the relatively high affinity for the various glycolipid/glycoprotein receptors. An example of this is the substitution of N-acetyl-D-glucosamine by (1R,2R)-trans-1, 2-cyclohexanediol. This chiral compound has only two hydroxyl groups whereas N-acetyl-D-glucosamine has four. As a result of the C2 symmetry of this diol, both hydroxyl groups are equivalent. This component therefore can be employed without protective groups since it is irrelevant which of the two hydroxyl groups is linked first. The product thus obtained can be employed directly, i.e., without protective group modification, for the next linkage. As a result of the reduced number of oxygen atoms, the hydroxyl groups of this diol have a substantially higher reactivity than those of N-acetyl-D-glucosamine, which also leads to a reduced number of stages and to higher yields.

The two hydroxyl groups of (1R,2R)-trans-1,2-cyclohexanediol have the same stereochemistry as the 3- and 4-hydroxyl groups of N-acetyl-D-glucosamine. The carbohydrate mimetic thus obtained has an affinity both to E- and P-selectin which is three times higher than sialyl-Lewis-X. In addition, both the N-acetyl group in the 2-position and the other hydroxyl groups are superfluous or even inconvenient for selectin binding. All of the carbohydrate mimetics according to the invention possess these same characteristics. A further important aspect of the mimetics described here is that the glycosidic bonds are acetals, which can be cleaved both by acid and by glycosidases.

As described here, the replacement of a glycosidic bond with an ether bond results in a higher stability of these mimetics. This may be particularly important for pharmaceutical compositions administered orally. In contrast, where a glycosidic bond is replaced by an ether bond does not create, the problems of a stereoselective linkage do not apply since primary alcohols are involved. The ether bond of the alcohol and activated group is linked under phase-transfer conditions in a two-phase system, e.g., in the presence of toluene and aqueous sodium hydroxide solution. This preferably takes place with addition of alkyl carbonates and crown ethers and deprotonation of the alcohol by a strong base in an aprotic solvent, such as DMF, DMSO, $CH_2Cl_2$. An example is the substitution of a sugar by pentaerythritol or glycerol. If D-galactose is replaced by glycerol and the remaining primary hydroxyl group is sialylated, the synthetic α-sialoside (18α) has an unexpectedly higher binding affinity both to E- and P-selectin than the β-sialoside (18β). α-Sialosides have additional advantages over β-sialosides because α-sialosides of sialidases cannot be cleaved and are distinctly more stable to dilute mineral acid (Kuhn, Lutz, MacDonald, *Chem. Ber.* 611–617, (1966)).

The compounds according to the invention, e.g., those of formula I, can be prepared from commercially available components containing at least 2 adjacent functional groups such as ethylene glycol, glycerol, (1R,2R)-trans-1,2-cyclohexanediol (Fluka) or, a D-threitol derivative having suitable radicals on the two primary hydroxyl groups (e.g., compound 7). In the case of a D-threitol derivative, commercially available (−)-2,3-O-isopropylidene-D-threitol is dialkylated and then deisopropylidenated. The reaction of these compounds with at most one equivalent of a glycosyl donor (e.g., tetraacetylgalactosyl trichloracetimidate in an aprotic solvent with acid catalysis; R. R. Schmidt, *Angew. Chem.* 98: 213–236 (1986)), of a dicarboxylic acid monoester (e.g., monomethyl adipate using DCC and DMAP in dichloromethane), or of a spacer triflate (e.g., the triflate of monoallylated propanediol in dichloromethane using potassium carbonate acid crown ether or under phase transfer conditions using tetrabutylammonium bromide and sodium hydroxide solution), gives the monoglycosylated product or monoacylated or monoalkylated product in high yields. In particular, the compounds according to the invention can be prepared by means of activated groups, such as triflates, tosylates, mesylates, bromides, iodides, chlorides, active esters, carbolic acid chlorides, carboxylic acid imidazolides and/or carboxylic anhydrides. Following this, the second hydroxyl group is glycosylated (e.g. with perbenzylated gluconic acid) or alkylated (e.g. with the monotriflate of perbenzylated dulcitol). The fully protected, distributed diol (or polyol) thus obtained is provided with an acidic function after removal of the allyl protective group or of the acetyl groups. For example, this can be N-acetylneuraminic acid, lactic, glycolic, glyceric or citric acid. After removal of all protective groups the biologically active compounds according to the invention are obtained.

If the compounds according to the invention are employed as anti-adhesion therapeutics, in the case of inflammation they should prevent the ELAM-1 receptors binding to stimulated endothelial cells on sialyl-Lewis-X structures on the surface of leucocytes. In the case of influenza therapy, the receptor blockers prevent attachment of viruses to the neuraminic acid on the cell surface and thus also the endocytosis of the virus particles. The receptors which recognize the carbohydrate mimetics are preferably those which are expressed on the cell surface, e.g., of mammalian cells, including human cells, bacterial cells or viruses. Receptors which recognize hormones or toxins are also preferred. Those cell surface receptors which belong to the selectin class are particularly preferred. The receptors expressed in inflammatory disorders are very particularly preferred, for example Leu-8 (=L-selectin=gp90$^{mel}$=LAM-1=LEC-CAM-1), ELAM-1 (=E-selectin) and GMP-140 (=P-selectin=CD62=PADGEM).

The present invention involves the synthesis of complex carbohydrate mimetics in which N-acetylglucosamine is replaced by R—CHOH—CHOH—R, the stereochemical arrangement of the hydroxyl groups, in the case of chiral compounds, corresponding to that of N-acetylglucosamine (e.g., ethylene glycol, glycerol, (1R,2R)-trans-1,2-cyclohexanediol, D-threitol, or 1,2-dideoxyglucose). In addition, galactose can be replaced by a spacer of suitable length or an open-chain compound having suitable functional groups (e.g., propanediol, glycerol having a free or substituted secondary OH group, or pentaerythritol having free or substituted hydroxyl groups). Furthermore, α-glycosidically linked neuraminic acid can be replaced by β-glycosidically linked acids or by other suitable acids (e.g., cinchonic acid, citric acid, glycolic acid, or lactic acid). The substitution of the αNANA-(2→3)-βGal unit by a suitable radical (e.g., mucic acid) is also possible. Fucose can be replaced by other sugars (e.g., arabinose, rhamnose, D-galactose, but also by flucitol, mannitol, or pentaerythritol). The carbohydrate mimetics according to the invention have advantages over previously identified inhibitors of selectin binding because these mimetics have a smaller number of glycosidic bonds, a higher affinity for E- and/or P-selectins and are simpler chemically, which facilitates a cheaper and simpler synthesis.

Thus, the compound of formula I according to the invention is prepared by the method comprising the steps of (1) alkylating or glycosylating a functional group of an acceptor II

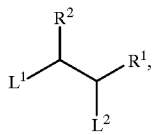

II containing at least two adjacent functional groups $L^1$ and $L^2$ and containing the substituents $R^1$ and $R^2$, with one equivalent of a donor III bearing at least two functional groups $L^3$ and $L^4$

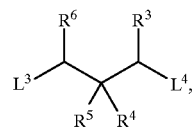

III one functional group $L^3$ of which is protected, if necessary, and the other functional group $L^4$ of which is optionally present in activated form, to achieve intermediate compound IV;

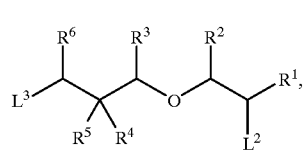

IV (2) alkylating, acylating or glycosylating the unprotected functional group $L^2$ of intermediate compound IV, with donor V having an activated functional group $L^5$ $$Z\text{-}L^5 \qquad V,$$

the other functional groups which carry protective groups, if necessary, to achieve intermediate compound VI;

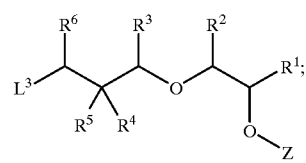

VI (3) selectively deprotecting and activating the functional group $L^3$ by reaction of intermediate compound VI with donor VII $$Y\text{-}L^6 \qquad VII,$$

which bears an activated functional group $L^6$ or protective groups, and (4) removing all protective groups to achieve a compound of formula I according to the invention, all variables having the meaning mentioned in the invention.

Alternatively, acceptor II can be reacted first with donor V and then with donor III to give the intermediate compound VI.

Despite their substantially lower molecular weight, the carbohydrate mimetics according to the invention can have a higher selectin binding affinity than their naturally occurring carbohydrate ligand counterparts. The cell adhesion assays described below demonstrate this higher affinity.

Leukocyte adhesion

The induced adhesion of leukocytes is quantified in the mesenterium of the rat using an intravital microscopic investigation technique (Atherton A. and Born G. V. R., Quantitative investigations of the adhesiveness of circulating polymorphonuclear leukocytes to blood vessel walls, *J. Physiol.* 222: 447–474 (1972); Seiffge, D., Methoden zur Untersuchung der Rezeptor-vermittelten Interaktion zwischen Leukozyten und Endothelzellen im Entzündungsgeschehen, [Methods for the investigation of the receptor-mediated interaction between leukocytes and endothelial cells in inflammatory phenomenal] Ersatz- und Ergänzungsmethoden zu Tierversuchen in der biomedizinischen Forschung [Substitution and replacement methods for animal experiments in biomedical research], Schöffl, H. et al., eds., Springer (1995) (in print)). Lasting anesthesia is initiated under inhalation ether anesthesia by intramuscular injection of urethane (1.25 mg/kg of body weight). After exposing vessels (femoral vein for the injection of substances and carotid artery for blood pressure measurement), catheters are tied into them. The corresponding transparent tissue (mesenterium) is then freed according to the standard methods known in the literature and arranged on the microscope stage and coated with warm liquid paraffin at 37° C. (Menger, M. D. and Lehr, H. A., Scope and perspectives of intravital microscopy-bridge over from in vitro to in vivo, *Immunology Today*, 14: 519–522 (1993)). The administration of the test substance to the animal is carried out intravenously (10 mg/kg). The experimental increase in blood cell adhesion is induced by cytokine activation by means of systemic administration of lipopolysaccharide (LPS, 15 mg/kg) 15 minutes after administration of test substance (Foster S. J., McCormick L. M., Ntolosi B. A. and Campbell D., Production of TNF-alpha by LPS-stimulated murine, rat and human blood and its pharmacological modulation, *Agents and Actions*, 38: C77–C79 (1993) 18.01. (1995)). The increased adhesion of leukocytes to the endothelium caused by this means is quantified by direct vital microscopy or with the aid of fluorescent dyes. All measuring operations are recorded by video camera and stored on a video recorder. Over a period of 60 minutes, the number of rolling leukocytes (i.e., all visible rolling leukocytes which are slower than the flowing erythrocytes) and the number of leukocytes adhering to the endothelium (residence period longer than 5 seconds) is determined every 10 minutes. After completion of the experiment, the anesthetized animals are painlessly put to sleep without excitation by systemic injection of T61. For analysis, the results of 8 treated animals with 8 untreated animals (control group) in each case are compared (data in percentages).

Based upon the results of the above described assay, the inventors determined that the inhibition of leucocyte adhesion [%] and the inhibition of leucocyte rolling [%] (in parentheses) after administration of the test substance (10 mg/kg) were as follows:

| Test substance: | | |
|---|---|---|
| 7e | 56.2 | (25.7) |
| 7f | 64.6 | (84.7) |
| 7g | 86.9 | (37.8) |
| 7h | 20.8 | (62.8) |

HL60 adhesion

Wells of a 96-well microtiter test plates (Nunc Maxisorb) are pretreated at room temperature for 2 hours with 100 µl of a goat anti-human IgG antibody (Sigma) diluted (1:100) in 50 mM tris pH 9.5. The antibody solution is removed, and the wells are washed once with PBS. Blocking buffer (0.1% gelatin, 1% BSA, 5% calf serum, 0.2 mM PMSF, 0.02% sodium azide) is added (150 µl per well) and left at room temperature for 1 hour. The blocking buffer is removed, and the wells are washed once with PBS. Cell culture supernatant from appropriately transfected and expressed COS cells are pipetted into the wells (100 µl per well) and incubated at room temperature for 2 hours. The cell culture supernatant is removed, and the wells are washed once with PBS. Binding buffer (50 mM HEPES, pH 7.5; 100 mM NaCl; 1 mg/ml BSA; 2 mM $MgCl_2$; 1 mM $CaCl_2$; 3 mM $MnCl_2$; 0.02% sodium azide, 0.2 mM PMSF) is added (20 µl per well). The test sample (5 µl per well) is added, and the wells are mixed by swirling the plates and incubated at room temperature for 10 minutes.

Fifty ml of an HL60 cell culture containing 200,000 cells/ml are centrifuged at 350 g for 4 minutes. The pellet is resuspended in 10 ml of RPMI 1640, and the cells are centrifuged again. To label the cells, 50 µl of BCECF-AM (Molecular Probes) are dissolved in 5 µl of anhydrous DMSO; 1.5 ml of RPMI 1640 are then added to the BCECF-AM/DMSO solution. The cells are resuspended using this solution and incubated at 37° C. for 30 minutes. After centrifugation at 350 g for two minutes, the labeled cell pellet is resuspended in 11 ml of binding buffer, and the resuspended cells are divided into 100 µl aliquots in the microtiter plate wells. The plate is allowed to stand at room temperature for 10 minutes to allow the cells to sediment on the bottom of the test plate, and thus have the chance to adhere to the coated plastic.

The assay is stopped by immersing the microtiter plate completely at an angle of 45° in the stop buffer (25 mM tris, pH 7.5; 125 mM NaCl; 0.1% BSA; 2 mM $MgCl_2$; 1 mM $CaCl_2$; 3 mM $MnCl_2$; 0.02% sodium azide). The stop buffer is removed from the wells by inversion, and the procedure is repeated twice more. The amount of BCECF-AM-labeled cells firmly adhering in the wells is quantified by a cytofluorimeter (Millipore), at a sensitivity setting of 4, an excitation wavelength of 485/220 nm and an emission wavelength of 530/250 nm.

Based upon the results of the above described assay, the inventors determined that the $IC_{50}$ values for E-selectin [µM] and P-selectin [µM] (in parentheses) were as follows:

| Test Substance: | | |
|---|---|---|
| 5a | 3.0 | (—) |
| 5b | 0.4 | (0.6) |
| 5c | 1.5 | (0.9) |
| 18α | 3.1 | (3.1) |
| 18β | 2.4 | (2.5) |
| 19α | — | (—) |
| 19β | 1.6 | (1.0) |
| 7f | 3.0 | (0.006) |
| 7g | 5.0 | (0.015) |
| 7h | 0.7 | (0.32) |
| 7i | 2.9 | (2.3) |

Selectins are unique glycoproteins expressed on endothelial and hematolymphoid cell surfaces that mediate intercellular adhesion. (Springer, *Nature*, 346: 425 (1989), which is herein incorporated by reference). Intercellular adhesion is involved in many pathological responses. For example, intercellular adhesion is a prerequisite for the movement of leukocytes from the blood to tissue sites where immune reactions and inflammation occur. By "inflammation" is meant reactions of both the specific and non-specific defense systems. A specific defense system reaction is a specific immune system reaction to an antigen. Examples of specific defense system reactions include antibody response to antigens, such as viruses, and delayed-type hypersensitivity. A non-specific defense system reaction is an inflammatory response mediated by leukocytes generally incapable of immunological memory. Such cells include macrophages, eosinophils and neutrophils.

The synthetic analogs according to the present invention are all carbohydrate ligand mimetics specific for the known selectins. Accordingly, these derivatives can inhibit the binding of selectins to their naturally occurring carbohydrate ligand counterparts, and thus inhibit intercellular adhesion. A ligand mimetic is a molecule that conformationally and functionally serves as a substitute for the natural ligand recognized by a selectin receptor.

Thus, in one embodiment, the invention relates to pharmaceutical compositions for inhibiting the binding of a selectin to a carbohydrate ligand on a cell expressing such a carbohydrate ligand. By the term "cell expressing carbohydrate ligand" is meant that a selectin-specific carbohydrate ligand is produced by cells associated with a specific condition and that production can be detected by any known method, for instance, by direct assays of mRNA transcript. Such cells include but are not limited to bacteria, viruses, white blood cells and cancer cells. White blood cells include but are not limited to leukocytes, lymphocytes and neutrophils. Cancer cells include but are not limited to those cells associated with colorectal, breast, ovarian and prostate cancer.

The pharmaceutical compositions according to the invention are prepared by bringing a carbohydrate mimetic according to the present invention into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in *Remington's Pharmaceutical Sciences*, 15th ed. Easton: Mack Publishing Co., 1405–1412, 1461–1487 (1975) and *The National Formulary XIV.*, 14th ed. Washington: American Pharmaceutical Association (1975), the contents of which are hereby incorporated by reference. The pH and exact concentration of the various components of the pharmaceutical composition are adjusted according to routine skills in the art. See *Goodman and Gilman's The Pharmacological Basis for Therapeutics* (7th ed.).

In another embodiment, the invention relates to a method of inhibiting the binding of a selectin to a carbohydrate ligand on a cell expressing such a carbohydrate ligand. This method involves administering to a subject a therapeutically effective dose of a pharmaceutical composition containing the compounds of the present invention and a pharmaceutically acceptable carrier. "Administering" the pharmaceutical composition of the present invention may be accomplished by any means known to the skilled artisan. By "subject" is meant any mammal, preferably a human.

The pharmaceutical compositions are preferably prepared and administered in dose units. Solid dose units are tablets, capsules and suppositories. For treatment of a patient, depending on activity of the compound, manner of administration, nature and severity of the disorder, age and body weight of the patient, different daily doses are necessary. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention are in general administered topically, intravenously, orally or parenterally or as implants, but even rectal use is possible in principle. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of present methods for drug delivery, see Langer, *Science,* 249: 1527–1533 (1990), which is incorporated herein by reference.

The pharmaceutical compositions according to the invention may be administered locally or systemically to control tissue damage associated with selectin-mediated injuries. Moreover, because of the specificity of such derivatives for sites of inflammation, these compositions will be more effective and less likely to cause complications when compared to traditional anti-inflammatory agents. In the case of influenza therapy, the pharmaceutical compositions can inhibit the binding of viruses to the neuraminic acid on the surface of target cells and thus prevent the endocytosis of the virus particle. Other treatable selectin-mediated diseases include autoimmune diseases (e.g., rheumatoid arthritis, multiple sclerosis, inflammatory bone disorders, lupus, myasthenia gravis, allergies, osteoarthritis, asthma, contact dermatitis, psoriasis, adult respiratory distress syndrome, and transplant rejection), infections (e.g., rhinitis, influenza, *Helicobacter pylori* infection, malaria, and septic shock), cancers (e.g., colorectal, breast, ovaries, and prostate), central nervous system disorders (e.g., stroke, trauma), reperfusion injuries (e.g., myocardial infarct, angioplasty, unstable angina, and systemic shock), and osteoporosis, wounds and severe burns.

By "therapeutically effective dose" is meant the quantity of a compound according to the invention necessary to prevent, to cure or at least partially arrest the symptoms of the disease and its complications. Amounts effective for this use will, of course, depend on the severity of the disease and the weight and general state of the patient. Typically, dosages used in vitro may provide useful guidance in the amounts useful for in situ administration of the pharmaceutical composition, and animal models may be used to determine effective dosages for treatment of particular disorders. Various considerations are described, e.g., in Gilman et al. (eds.) (1990) *Goodman and Gilman's: The Pharmacological Bases of Therapeutics,* 8th ed., Pergamon Press; and *Remington's Pharmaceutical Sciences,* 17th ed. (1990), Mack Publishing Co., Easton, Pa., each of which is herein incorporated by reference.

In another embodiment, the present invention relates to an antibody. The term "antibody" refers to both poly- and monoclonal antibodies and fragments thereof. Indeed, the compounds according to the present invention are suitable for the production of antibodies for the diagnostic determination of ligands which are not accessible, not immunogenic enough or unknown. In many autoimmune disorders and tumors, certain ligands or antigens on the cell membrane are highly regulated. However, these are frequently unknown, cannot be isolated in pure form or are not sufficiently immunogenic to be able to produce antibodies therefrom. The compounds according to the present invention can be used for the production of antibodies that cross-react with epitopes of the natural, unknown or inaccessible ligands.

Polyclonal antibodies against the compounds of the present invention can be produced in various ways using techniques well-understood by those having ordinary skill in the art. Details of these techniques are described in "Production of Polyclonal Antisera in Rabbits, Rats, Mice and Hamsters" in *Current Protocols in Immunology*, Coligan, J. E., et al., eds., National Institutes of Health, section 2.4.1 (1992), which is hereby incorporated by reference.

Monoclonal antibodies against the compounds of the present invention can be produced in various ways using techniques well-understood by those having ordinary skill in the art. Details of these techniques are described in *Antibodies: A Laboratory Manual*, Harlow et al. Cold Spring Harbor Publications, p. 726 (1988), which is hereby incorporated by reference. The monoclonal antibodies according to this invention are multiplied according to in vitro and in vivo methods well-known in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements, e.g., feeder cells, such as normal mouse peritoneal exudate cells, spleen cells, bone marrow macrophages or the like. In vitro production provides relatively pure antibody preparations and allows scale-up to give large amounts of the desired antibodies. Techniques for large scale hybridoma cultivation under tissue culture conditions are known in the art and include homogenous suspension culture, e.g., in an airlift reactor or in a continuous stirrer reactor or immobilized or entrapped cell culture.

Large amounts of the monoclonal antibody of the present invention may also be obtained by multiplying hybridoma cells in vivo. Cell clones are injected into mammals which are histocompatible with the parent cells, e.g. syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the mammal.

In accordance with the present invention, fragments of the monoclonal antibody of the invention can be obtained from the monoclonal antibody produced as described above, by methods which include digestion with enzymes such as pepsin or papain and/or cleavage of disulfide bonds by chemical reduction. Alternatively, monoclonal antibody fragments encompassed by the present invention can be synthesized using an automated peptide synthesizer as supplied by Applied Biosystems, Multiple Peptide Systems, etc., or they may be produced manually, using techniques well known in the art. See Geysen, et al. *J. Immunol. Methods* 102: 259–274 (1978), hereby incorporated by reference.

In addition to the diagnostic and detection applications, therapeutic applications are also conceivable for the antibodies produced in this manner (A. N. Houghton, D. A. Scheinberg, *Semin. Oncol.* 13: 165–179 (1986); W. C. Eckelmarm, *In Vivo Diagnosis and Therapy of Human Tumors with Monoclonal Antibodies*; Pergamon Press, London 1988; M. H. Ravindranath, D. L. Morton, R. F. Irie, *Cancer Res.* 49: 3891–3897 (1989)).

In another embodiment, the invention relates to a diagnostic kit for detecting a carbohydrate ligand that binds to a selectin. This kit comprises the antibody of the present invention. The kit may also comprise a detectable label and a set of written instructions for using such a kit. Such a kit may comprise a receptacle being compartmentalized to receive one or more containers such as vials, tubes and the like, such containers holding separate elements of the invention.

In another embodiment, the antibody of the invention is used in a method of detecting in a sample a carbohydrate ligand. This in vitro assay involves contacting a sample suspected of containing a carbohydrate ligand-expressing cell with the above described antibody, which is detectably labeled. The carbohydrate ligand-expressing cell that binds to the antibody is then detected. By "sample" is meant any body fluid or tissue, including blood, urine, saliva, spinal fluid, semen, peritoneal fluid, and tissue from any part of the body, such as any organ, muscle or skin. A wide variety of detectable labels may be used, and the antibody may be labeled by any one of several methods. A common method of detection is the use of autoradiography with $^{3}$H, $^{125}$I, $^{35}$S, $^{14}$C or $^{32}$P labeled compounds or the like. For instance, antibodies can be iodinated by contact with sodium or potassium iodide and a chemical oxidizing agent such as sodium hypochlorite, or an enzymatic oxidizing agent, such as lactoperoxidase. The choice of radioactive isotope depends on research preferences due to ease of synthesis, varying stability, and half lives of the selected isotopes.

Non-radioactive labels including fluorophores, chemiluminescent agents, and enzymes may be employed. The choice of label depends on sensitivity required, ease of conjugation with the compound, stability requirements, and available instrumentation. Non-radioactive labels are often attached by indirect means. Generally, a ligand molecule (e.g., biotin) is covalently bonded to the molecule. The ligand then binds to an anti-ligand (e.g., streptavidin) molecule which is either inherently detectable or covalently bound to a signal system, such as a detectable enzyme, a fluorescent compound, or a chemiluminescent compound. Ligands and anti-ligands may be varied widely.

This assay can be a competitive or sandwich assay, or any assay well-known to the artisan which depends on the formation of an antibody-antigen complex. For purposes of this invention, the antibody can be immobilized or labeled. Many carriers are known to the skilled artisan to which the antibody of the present invention can be bound for immobilization. Where required, derivatization techniques can be used for immobilizing the antibody on a substrate. Well-known carriers include glass, polystyrene, polypropylene, polyethylene, dextran, nylon, amylases, natural and modified celluloses, etc. The carrier can be either soluble or insoluble. Immunoassays encompassed by the present invention include, but are not limited to those described in U.S. Pat. No. 4,367,110 (double monoclonal antibody sandwich assay); Wide et al., Kirkham and Hunter, eds. *Radioimmunoassay Methods*, E. and S. Livingstone, Edinburgh (1970); U.S. Pat. No. 4,452,901 (western blot); Brown et al., *J. Biol. Chem.* 255: 4980–4983 (1980) (immunoprecipitation of labeled ligand); and Brooks et al., *Clin. Exp. Immunol.* 39: 477 (1980) (immunocytochemistry).

In another embodiment, the invention relates to a method of detecting in a sample a selectin-expressing cell. This in vitro assay involves contacting an above described sample suspected of containing a selectin-expressing cell with a compound according to the invention that is detectably labeled. The selectin-expressing cell that binds to the detectably labeled compound is then detected. By the term "selectin-expressing cell" is meant that a selectin is produced by a cell and that production can be detected by any known method, for instance, by direct assays of mRNA transcripts. Such cells include but are not limited to endothelial cells and various circulating cells of the hematolymphoid system. In certain assays, the "cell" may be a membrane preparation of a cell. Assays included in the present invention may involve flow cytometry and a fluorescence-activated cell sorter, according to methods well-known in the art. Parks et al., *Fund. Immunol.*, Paul, ed., Raven Press, 2d ed. (1989), which is incorporated herein by reference.

Other assays involve binding the compound of the present invention or the cells to be analyzed to a solid surface. Many methods for immobilizing biomolecules on solid surfaces are known in the art. For instance, the solid surface may be a membrane (e.g., nitrocellulose), a microtiter dish or a bead. The bound molecule may be covalently or noncovalently attached through unspecific bonding. The manner of linking a wide variety of compounds to various surfaces is well-known and well-documented in the literature. See, e.g., Chibata, *Immunological Enzymes*, Halsted Press (1978) and Cuatvecasos, *J. Biol. Chem.* 245: 3059 (1970), which are incorporated herein by reference.

In the assay of the present invention for detecting selectin on selectin-expressing cells, the compound of the invention is labeled by methods well-known in the art. A common method involves the use of radioisotopes such as $^3$H, $^{125}$I, $^{35}$S, $^{14}$C or $^{32}$P. Detection is accomplished by autoradiography. Non-radioactive labels include the covalent binding of biotin to the compound of the present invention. Biotin is then bound to an anti-ligand such as streptavidin, which is either inherently labeled or bound to a signal system, such as a detectable enzyme, a fluorescent or chemiluminescent compound.

Without further elaboration, it is believed that one skilled in the art can, using the preceding description, utilize the present invention to its fullest extent. The following examples are merely illustrative and not limitative of the remainder of the disclosure in any way whatsoever.

| Abbreviations used | |
|---|---|
| Ac | Acetyl |
| All | Allyl |
| Bn | Benzyl |
| DMF | Dimethylformamide |
| DMSO | Dimethyl sulfoxide |
| DMTr | 4,4'-Dimethoxytrityl |
| Hex | n-Hexyl |
| NANA | N-Acetylneuraminic acid |
| PdC | Palladium on active carbon |
| TBABr | Tetrabutylammonium bromide |
| Tf$_2$O | Trifluoromethanesulfonic anhydride |
| TMSOTf | Trimethylsilyl trifluoromethanesulfonate |

EXAMPLE 1 a) Synthesis of ethylene glycol mono-O-2,3,4-tri-O-acetyl-6-O-benzyl-β-D-galactopyranoside (2a)

A 0.1 M solution of TMSOTf (2.8 ml) is added dropwise to a solution of O-(2,3,4-tri-O-acetyl-6-O-benzyl-α/β-D-galactopyranosyl) trichloroacetimidate (1.5 g, 2.77 mmol) and ethylene glycol (310 μl, 5.55 mmol) in a little diethyl ether/dichloromethane (1:1). After 30 minutes, the mixture is neutralized with solid sodium hydrogen carbonate (0.5 g), filtered and concentrated in vacuo. After flash chromatography [toluene/acetone (4:1)], compound 2a (890 mg, 73%) is obtained.

$^1$H-NMR (300 MHz, CDCl$_3$: δ=1.98, 2.07, 2.08 (3s, 9H, 3OAc), 2.35 (bs, 1H, OH), 5.02 (dd, 1H, 3-H), 5.21 (dd, 1H, 2H), 5.45 (dd, 1H, 4-H).

b) Synthesis of ethylene glycol O-(2,3,4-tri-O-benzyl-α-L-fucopyranosyl)-2,3,4-tri-O-acetyl-6-O-benzyl-β-D-galactopyranoside (3a)

A solution of 2a (865 mg, 1.96 mmol) is stirred for 1 hour with molecular sieve 4A, TBABr (218 mg, 968 mmol) and CuBr$_2$ (1.18 g, 529 mmol) in DMF/dichloromethane (1:5, 48 ml). A solution of thioethyl O-2,3,4-tri-O-benzyl-β-L-fucopyranoside (1.41 g, 2.94 mmol) in dichloromethane (2 ml) is then added. After 24 hours, the mixture is filtered through kieselguhr, rinsed with dichloromethane and washed with sodium hydrogen carbonate followed by water. Concentration and chromatography (hexane/ethyl acetate 4:1) yields 3a (1.3 g, 77%).

$^1$H-NMR (300 MHz, CDCl$_3$: δ=1.08 (d, 3H, 6-H$_{fuc}$), 1.96, 1.99, 2.03 (3s, 9H, 3OAc), 5.16 (dd, 1H, 2-H$_{gal}$), 5.41 (dd, 1H, 4-H$_{gal}$).

c) Synthesis of ethylene glycol O-(2,3,4-tri-O-benzyl-L-α-fucopyranosyl)-6-O-benzyl-β-D-galactopyranoside (4a)

A solution of 3a (1.3 g, 1.52 mmol) in methanol (100 ml) is treated with 1 M sodium methoxide solution. After 3 hours, the mixture is neutralized with Amberlite IR-120, filtered and concentrated in vacuo. Flash chromatography (dichloromethane/methanol 20:1) yields 4a (852 mg, 77%).

$^1$H-NMR (300 MHz, CDCl$_3$): δ=1.10 (d, 3H, 6-H$_{fuc}$), 2.48, 2.53 (2d, 2H, 2OH).

d) Synthesis of ethylene glycol O-(α-L-fucopyranosyl)-(5-acetamido-3,5-dideoxy-D-glycero-α-D-galacto-2-nonulopyranosylonic acid)-(2-3)-β-D-galactopyranoside (5a)

N-Iodosuccinimide (770 mg, 3.42 mmol) and trifluoromethanesulfonic acid (30 μl, 0.34 mmol) are added at −40° C. to a mixture of 4a (832 mg, 1.14 mmol) and methyl S-(methyl-5-acetamido-2,4,7,8,9-penta-O-acetyl-3,5-dideoxy-D-glycero-D-galacto-2-nonulopyranosylonate) (891 mg, 1.71 mmol) and molecular sieve (3A) in dichloromethane/acetonitrile (18 ml, 5:4). After 2 hours, the deep-red solution is neutralized with sodium hydrogen carbonate (0.5 g) and then filtered and washed with dichloromethane (100 ml). It is extracted by shaking with 20% strength sodium thiosulfate solution (100 ml) and water (50 ml), dried over sodium sulfate, filtered and concentrated. The residue is dissolved in methanol (40 ml) and treated with 1 M sodium methoxide solution. After 4 hours, the mixture is neutralized with Amberlite IR-120, filtered and concentrated in vacuo. The lactones are isolated by flash chromatography (dichloromethane/methanol 15:1[10:1[9:1[8:1[7:1), taken up in methanol/dioxane (6:1, 66 ml), treated with palladized carbon (10%, 350 mg) and hydrogenated under a hydrogen atmosphere for 24 hours. The mixture is filtered, the filter cake is rinsed with methanol and the filtrate is concentrated in vacuo. The residue is taken up with methanol (25 ml) and treated with 1 M sodium hydroxide solution (5 ml). Neutralization with Amberlite IR-120 and concentration in vacuo yield, after Biogel chromatography, compound 5a (190 mg, 41%).

$^1$H-NMR (300 MHz, D$_2$O): δ=1.03 (d, 3H, 6-H$_{fuc}$), 1.62 (dd, 1H, 3-H$_{nana}$), 1.85 (s, 3H, NAc), 2.58 (dd, 1H, 3-H$_{nana}$), 4.34 (d, 1H, 1-H$_{gal}$), 4.75 (d, 1H, 1-H$_{fuc}$).

EXAMPLE 2 a) Synthesis of (1R,2R)-trans-1,2-cyclohexanediol-mono-O-2,3,4-tri-O-acetyl-6-O-benzyl-β-D-galactopyranoside (2b)

Compound 2b is synthesized analogously to 2a.

b) Synthesis of (1R,2R)-trans-cyclohexanediol O-(2,3,4-tri-O-benzyl-α-L-fucopyranosyl)-2,3,4-tri-O-acetyl-6-O-benzyl-β-D-galactopyranoside (3b)

Compound 3b is synthesized analogously to 3a.

c) Synthesis of (1R,2R)-trans-cyclohexanediol O-(2,3,4-tri-O-benzyl-α-L-fucopyranosyl)-6-O-benzyl-β-D-galactopyranoside (4b)

Compound 4b is synthesized analogously to 4a.

d) Synthesis of (1R,2R)-trans-1,2-cyclohexanediol-O-(α-L-fucopyranosyl)-(5-acetamido-3,5-dideoxy-D-glycero-α-D-galacto-2-nonulopyranosylonic acid)-(2-3)-β-D-galactopyranoside (5b)

Compound 5b is prepared analogously to 5a.

$^1$H-NMR (300 MHz, D$_2$O): δ=0.98 (d, 3H, 6-H$_{fuc}$), 1.04 (m, 4H, 4-H$_{cyclohex}$, 5-H$_{cyclohex}$), 1.51, 1.93 (2m, 4H, 3-H$_{cyclohex}$, 6-H$_{cyclohex}$), 1.68 (dd, 1H, 3-H$_{nana}$), 1.84 (s, 3H, NAc), 2.55 (dd, 1H, 3-H$_{nana}$), 3.94 (dd, 1H), 4.38 (d, 1H, 1-H$_{gal}$), 4.45 (m, 1H, 5-H$_{fuc}$), 4.79 (d, 1H, 1-H$_{fuc}$).

EXAMPLE 3 a) Synthesis of 1,4-O-n-hexyl-2,3-O-isopropylidene-D-threitol (6)

Bromohexane (13 ml, 92.4 mmol) and, after 24 hours, a further 13 ml is added with stirring to a mixture of (−)-2,3-O-isopropylidene-D-threitol (5.0 g, 30.8 mmol), tetrabutylammonium hydrogen sulfate (5.23 g, 15.4 mmol), toluene (60 ml) and 50% strength sodium hydroxide solution (50 ml). After a total of 48 hours, water (100 ml) and hexane (200 ml) are added, the mixture is stirred for 10 minutes, and the organic phase is separated off and washed with water (50 ml). Dry ice is added to the organic phase until the wash water has a neutral reaction. The organic phase is concentrated and purified by means of flash chromatography (hexane/ethyl acetate 8:1). Yield: (8.3 g, 81%).

$^1$H-NMR (300 MHz, CDCl$_3$): δ=0.89 (2dd, 6H, 2Me), 1.29 (m, 12H, 6 CH$_2$), 1.42 (s, 6H, 2Me$_{isopropylidene}$), 1.58 (m, 4H, 2CH$_2$), 3.47 (m, 4H, 2CH$_2$), 3.56 (m, 4H, 2CH$_2$), 3.97 (m, 2H, 2-H, 3-H).

b) Synthesis of 1,4-O-hexyl-2,3-D-threitol (7)

A solution of 6 (8.3 g, 24.96 nmol) in 50% strength acetic acid (400 ml) is stirred at 90° C. for 4 hours. The mixture is concentrated in vacuo and purified on a short silica gel column (toluene/acetone 5:1). Yield: (7.0 g, 96%).

c) Synthesis of 1,4-O-n-hexyl-2,3-D-threitol mono-O-2,3,4-tri-O-acetyl-6-O-benzyl-β-D-galactopyranoside (2c)

Compound 2c is synthesized from 7 in analogy to 2a.

$^1$H-NMR (300 MHz, CDCl$_3$): δ=0.88 (m, 6H, 2 Me), 1.29 (m, 12H, 6CH$_2$), 1.97, 2.04, 2.04 (3s, 9H, 3OAC), 2.88 (d, 1H, OH), 5.01 (dd, 1H, 3-H), 5.16 (dd, 1H, 2-H), 5.46 (dd, 1H, 4-H).

d) Synthesis of 1,4-O-n-hexyl-2,3-D-threitol)-(2,3,4-tri-O-benzyl-α-L-fucopyranosyl)-2,3,4-tri-O-acetyl-O-benzyl-β-D-galactopyranoside (3c)

Compound 3c is synthesized analogously to 3a.

$^1$H-NMR (300 MHz, CDCl$_3$): δ=1.08 (d, 3H, 6-H$_{fuc}$), 1.96, 1.99, 2.03 (3s, 9H, 3OAC), 5.16 (dd, 1H, 2-H$_{gal}$), 5.41 (dd, 1H, 4-H$_{gal}$).

e) Synthesis of 1,4-O-n-hexyl-2,3-D-threitol O-(2,3,4-tri-O-benzyl-α-L-fucopyranosyl)-6-O-benzyl-β-D-galactopyranoside (4c)

Compound 4c is synthesized analogously to compound 4a.

f) Synthesis of 1,4-O-n-hexyl-2,3-D-threitol O-(α-L-fucopyranosyl)-(5-acetamido-3,5-dideoxy-D-glycero-α-D-galacto-2-nonulopyranosylonic acid)-(2[3)-β-D-galactopyranoside (5c)

Compound 5c is synthesized analogously to 5a.

$^1$H-NMR (300 MHz, D$_2$O): δ=0.72 (m, 6H, 2Me), 1.04 (d, 3H, 6-H$_{fuc}$), 1.15 (m, 12H, 6CH$_2$), 1.40 (m, 4H, 2CH$_2$), 1.74 (dd, 1H, 3-H$_{nana}$), 1.88 (s, 3H, NAc), 2.58 (dd, 1H, 3-H$_{nana}$), 4.38 (d, 1H, 1-H$_{gal}$), 4.91 (d, 1H, 1-H$_{fuc}$).

EXAMPLE 4 a) Synthesis of D-α/β-isopropylideneglycerol/γ-allyl ether (8)

D-α/β-Isopropylideneglycerol is added at 25 to 30° C. to a mixture of DMF (80 ml), allyl bromide (8.18 ml, 96.72 mmol) and sodium hydride (2.51 g, 104.78 mmol). After 30 minutes, water (500 ml) is added. After 18 hours, methanol (1.5 ml) is added. The aqueous phase is extracted with ether (3×300 ml) and the combined organic extracts are washed with water (3×300 ml), concentrated and chromatographed (hexane/ethyl acetate 5:1) to obtain compound 8. Yield: (11.78 g, 71%).

b) Synthesis of (R)-3-allyloxy-1,2-propanediol (9)

A mixture of 8 (11.78 g, 68.5 mmol) and 50% strength acetic acid (500 ml) is warmed at 60° C. for 3 hours. It is then concentrated in vacuo and the residue is subsequently distilled 3 times with toluene to obtain compound 9. Yield: (8.5 g, 95%).

c) Synthesis of (R)-3-allyloxy-1-dimethoxytrityloxy-2-propanol (10)

A mixture of compound 9 (8.3 g, 63.36 mmol), pyridine (150 ml) and dimethoxytrityl chloride (21.5 g, 63.36 mmol) is stirred for 30 minutes and concentrated, the residue is dissolved in dichloromethane (300 ml) and the solution is washed with 1.2% strength sodium hydrogen carbonate solution (500 ml) and water (3×100 ml). The organic phase is concentrated and chromatographed (hexane/ethyl acetate 3:1+1% triethylamine).

Yield: (26.1 g, 95%).

d) Synthesis of (R)-3-Allyloxy-2-benzyloxy-1-dimethoxytrityloxypropane (11)

Compound 10 (22 g, 50.69 mmol) is added to a mixture of DMF (100 ml), benzyl bromide (10.4 g, 60.83 mmol) and sodium hydride (1.58 g, 65.9 mmol). After 30 minutes, water (400 ml) is added. After 18 hours, methanol (10 ml) is added.

The mixture is extracted with ether (3×250 ml) and the combined organic extracts are washed with water (3×250 ml). Concentration and flash chromatography (hexane/ethyl acetate 7:1→5.5:1→4:1) yield compound 11 (23.47 g, 88%).

e) Synthesis of (R)-3-Allyloxy-2-benzyloxy-1-propanol (12)

Compound 11 (23.47 g, 44.8 mmol) is treated for 15 minutes with 50% strength acetic acid (500 ml). Concentration in vacuo and chromatography (hexane/ethyl acetate 5:1→4:1→3:1→2:1) yield compound 12 (8.95 g, 90%).

f) Synthesis of 3-allyloxy-2-benzyloxy-1-trifluoromethanesulfonyloxypropane (13a)

Trifluoromethanesulfonic acid (5.95 ml, 36.3 mmol) is added dropwise at −30° C. to a mixture of dichloromethane (130 ml) and pyridine (3.19 g, 40.3 mmol). Compound 12 (8.95 g, 40.3 mmol) in dichloromethane (60 ml) is then added dropwise at −25° C. The mixture is allowed to come to room temperature and is concentrated in vacuo, and the residue is chromatographed (hexane/ethyl acetate 6:1). Compound 13a (13 g, 91%) is obtained.

g) Synthesis of 3-allyloxy-2-benzyloxy-1-(O-(1R,2R)-trans-1,2-cyclohexanediol)propanol (14a)

Compound 13a (3.05 g, 8.6 mmol) and 50% strength aqueous sodium hydroxide solution (8 ml) are added to a mixture of (1R,2R)-trans-1,2-cyclohexanediol (1 g, 8.6 mmol) and tetrabutylammonium bromide (1.39 g, 4.3 mmol) in toluene (80 ml). The mixture is stirred overnight, diluted with ether and washed with water, and the organic phase is neutralized with dry ice. Flash chromatography (hexane/ethyl acetate 4:1→3:1) yields compound 14a (1.8 g, 65%).

$^1$H-NMR (300 MHz, CDCl$_3$): δ=1.20 (m, 4H, 5-H$_{cyclohex}$, 6-H$_{cyclohex}$), 1.70, 2.0 (2m, 2×2 H, 3-H$_{cyclohex}$, 6-H$_{cyclohex}$) 3.04, 3.42 (2m, 2×1 H, 1-H$_{cyclohex}$, 2-H$_{cyclohex}$), 3.5–3.86 (m, 5H, 1,2,3-H$_{propane}$), 4.0 (m, 2H, CH$_2$=CH—C$\underline{H}_2$), 4.68 (2d, 2H, C$\underline{H}_2$Bn), 5.2 (m, 2H, C$\underline{H}_2$=CH—CH$_2$), 5.9 (m, 1H, CH$_2$—C$\underline{H}$—CH$_2$), 7.3 (m, 5H, Ph).

(h) Synthesis of 3-allyloxy-2-benzyloxy-1-(O-(1R,2R)-trans-1,2-cyclohexanediol)-(α-tribenzylfucopyranosyl)propanol (15a)

Compound 15a is synthesized analogously to 3a.

i) Synthesis of 3-hydroxy-2-benzyloxy-1-(O-(1R,2R)-trans-1,2-cyclohexanediol-(α-tribenzylfucopyranosyl)propanol (16a)

DBU (0.13 ml) and Wilkinson catalyst (0.48 g, 0.52 mmol) are added to a solution of 15a (3.84 g, 5.21 mmol) in ethanol/water (9:1, 100 ml). The mixture is boiled under reflux for 40 minutes and concentrated, and the residue was chromatographed on a short silica gel column (hexane/ethyl acetate 7:2). The residue (3.9 g) is dissolved in acetone/water (9:1, 20 ml) and treated with mercury(II) oxide (1.9 g) and a solution of mercury(II) chloride (1.9 g, 7.03 mmol) in acetone/water (9:1, 40 ml). After 3 hours, the reaction mixture is filtered off with suction through kieselguhr and rinsed with chloroform (200 ml). The filtrate is washed with 30% strength potassium iodide solution (3×30 ml). The organic phase is concentrated in vacuo. Flash chromatography (hexane/ethyl acetate 3:1[2:1) yields compound 16a (2.74 g, 76%).

$^1$H-NMR (300 MHz, CDCl$_3$): δ=1.06 (d, 3H, 6-H$_{fuc}$), 2.22 (6, 1H, OH), 4.97 (dd, 1H, 4-H$_{gal}$).

j) Synthesis of 3-(methyl 5-acetamido-2,4,7,8,9-penta-O-acetyl-3,5-dideoxy-D-glycero-α-D-galacto-2-nonulopyranosylonate)-2-benzyloxy-1-(O-(1R,2R)-trans-1,2-cyclohexanediol)-(α-tribenzylfucopyranosyl)propanol (17aα) and 3-(methyl 5-acetamido-2,4,7,8,9-penta-O-acetyl-3,5-dideoxy-D-glycero-β-D-galacto-2-nonulopyranosylonate)-2-benzyloxy-1-(O-(1R,2R)-trans-1,2-cyclohexanediol)-(β-tribenzylfucopyranosyl)propanol (17aβ)

Compound 16a (0.4 g, 0.57 mmol) is sialylated in acetonitrile as described in 5a. Medium-pressure chromatography (dichloromethane/methanol 80:1[50:1) yields 17aα (233 mg, 35%) and the corresponding β-sialoside 17aβ (120 mg, 18%). The use of dichloromethane as solvent and/or higher temperatures, at most room temperature, can increase the proportion of the β-glycoside.

k) Synthesis of 3-(5-acetamido-3,5-dideoxy-D-glycero-α-D-galacto-2-nonulopyranosylonic acid)-2-benzyloxy-1-(O-(1R,2R)-trans-1,2-cyclohexanediol)-(α-tribenzylfucopyranosyl)propanol (18α) and 3-(5-acetamido-3,5-dideoxy-D-glycero-β-D-galacto-2-nonulopyranosylonic acid)-2-benzyloxy-1-(O-(1R,2R)-trans-1,2-cyclohexanediol)-(β-tribenzyl-fucopyranosyl)propanol (18β)

The compounds 18α and 18β are deprotected as described in 5a.

18α: $^1$H-NMR (300 MHz, D$_2$O): δ=1.04 (d, 3H, 5-H$_{fuc}$), 1.60 (dd, 1H, 3-H$_{nana}$), 1.87 (s, 3H, NAc), 2.56 (dd, 1H, 3-H$_{nana}$), 4.88 (d, 1H, 1-H$_{fuc}$).

18β: $^1$H-NMR (300 MHz, D$_2$O): δ=1.03 (d, 3H, 6-H$_{fuc}$), 1.49 (dd, 1H, 3-H$_{nana}$), 1.88 (s, 3H, NAc), 2.23 (dd, 1H, 3-H$_{nana}$), 4.89 (d, 1H, 1-H$_{fuc}$).

EXAMPLE 5 a) Synthesis of 3-allyloxy-1-trifluoromethanesulfonyloxypropane (13b)

1. A mixture of 1,3-propanediol (10 ml, 138 mmol), allyl bromide (7.6 ml, 90 mmol), potassium carbonate (13.8 g, 100 mmol) and dibenzo)-18-crown-6 (21 mg, 0.6 ml) is stirred for 24 hours. The mixture is filtered, concentrated and chromatographed (hexane/ethyl acetate).

$^1$H-NMR (300 MHz, CDCl$_3$): δ=0.86 (m, 2H, CH$_2$), 2.46 (m, 1H, OH), 3.62 (m, 2H, CH$_2$), 3.76 (m, 2H, CH$_2$), 3.98 (m, 2H, C$\underline{H}_2$CH=CH$_2$), 5.20 (m, 2H, CH$_2$CH=C$\underline{H}_2$), 5.20 (m, 1H, CH$_2$C$\underline{H}_2$=CH$_2$).

2. Trifluoromethanesulfonate (0.54 ml, 3.32 mmol) is added dropwise at −30° C. to a mixture of dichloromethane (12 ml) and pyridine (0.3 mg, 3.7 mmol). 1-Allyloxy-3-propanol (430 mg, 3.7 mmol) in dichloromethane (6 ml) is then added dropwise at −25° C. The mixture is allowed to come to room temperature and is concentrated in vacuo, and the residue is chromatographed (hexane/ethyl acetate 6:1). Compound 13 b (0.56 g, 61%) is obtained.

b) Synthesis of 3-allyloxy-1-(O-(1R,2R)-trans-1,2-cyclohexanediol)propanol (14b)

Compound 14b is prepared from 13b analogously to 14a.

c) Synthesis of 3-allyloxy-1-(O-(1R,2R)-trans-1,2-cyclohexanediol)-(α-tribenzylfucopyranosyl)propanol (15b)

Compound 15b is synthesized analogously to 3a.

d) Synthesis of 3-hydroxy-1-(O-(1R,2R)-trans-1,2-cyclohexanediol)-(α-tribenzylfucopyranosyl)propanol (16b)

Compound 16b is synthesized analogously to 16a.

e) Synthesis of 3-(methyl 5-acetamido-2,4,7,8,9-penta-O-acetyl-3,5-dideoxy-D-glycero-α-D-galacto-2-nonulopyranosylonate)-1-(O-(1R,2R)-trans-1,2-cyclohexanediol)-(α-tribenzylfucopyranosyl)propanol (17bα) and 3-(methyl 5-acetamido-2,4,7,8,9-penta-O-acetyl-3,5-dideoxy-D-glycero-β-D-galacto-2-nonulopyranosylonate)-1-(O-(1R,2R)-trans-1,2-cyclohexanediol)-(β-tribenzylfucopyranosyl)propanol (17bβ)

Compounds 17bα and 17bβ are synthesized analogously to 17a or 5a.

f) Synthesis of 3-(5-acetamido-3,5-dideoxy-D-glycero-α-D-galacto-2-nonulopyranosylonic acid)-1-(O-(1R,2R)-trans-1,2-cyclohexanediol)-(α-tribenzylfucopyranosyl)propanol (19α) and 3-(5-acetamido-3,5-dideoxy-D-glycero-β-D-galacto-2-nonulopyranosylonic acid)-1-(O-(1R,2R)-trans-1,2-cyclohexanediol)-(β-tribenzylfucopyranosyl)propanol (19β)

Compounds 19α and 19β are synthesized analogously to 5a.

18bα: $^1$H-NMR (300 MHz, D$_2$O): δ=1.05 (d, 3H, 6H$_{fuc}$), 1.65 (dd, 1H, 3-H$_{nana}$), 1.86 (s, 3H, NAc), 2.58 (dd, 1H, 3-H$_{nana}$), 4.86 (d, 1H, 1-H$_{fuc}$).

18bβ: $^1$H-NMR (300 MHz, D$_2$O): δ=1.05 (d, 3H, 6H$_{fuc}$), 1.60 (dd, 1H, 3-H$_{nana}$) 1.90 (s, 3H, NAc), 2.25 (dd, 1H, 3-H$_{nana}$), 4.87 (d, 1H, 1-H$_{fuc}$).

EXAMPLE 6

The synthesis of the compounds 20α and 20β is carried out analogously to the compounds 18aα and 19aβ.

EXAMPLE 7 a) Synthesis of 4,6-isopropylidene-1,2-dideoxyglucose (1e)

A solution of tri-O-acetyl-D-glucal (30 g, 110.17 mmol) in dioxane (400 ml) is hydrogenated for 24 hours in a hydrogen atmosphere using palladized carbon (10%, 3 g). The mixture is filtered through kieselguhr and concentrated. To remove the acetyl groups, the residue is taken up in methanol (500 ml) and a 1 M sodium methoxide solution (6 ml) is added. After 90 minutes, the mixture is neutralized with Amberlite IR-120, filtered and concentrated in vacuo. The residue is coevaporated with toluene (3×250 ml) and taken up in DMF (500 ml). Dimethoxypropane (140 ml, 114.6 mmol) and p-toluenesulfonic acid (400 mg) are added to the solution. After 18 hours, triethylamine (3 ml) is added, and the mixture is stirred for a further 15 minutes and concentrated in a high vacuum. Chromatography (toluene/acetone 4:1) yields compound 1d (33 g, 80%).

$^1$H-NMR (300 MHz, CDCl$_3$) δ=1.41, 1.51 (2s, 6H, 2CH$_3$), 1.76 (ddd, 1H, 2-H), 2.0 (ddd, 1H, 2-H), 2.8 (d, 1H, OH), 3.16 (m, 1H, 5-H), 3.46 (dd, 11, 6-H), 3.53 (m, 1H, 1-H), 3.7 (dd, 1H, 6-H), 3.86 (dd, 14, 4-H), 3.96 (m, 1H, 5-H).

b) Synthesis of 4-allyloxy-1-hydroxybutyl-(1[3)-4,6-isopropylidene-1,2-dideoxyglucose (2e)

2e is synthesized analogously to 2a.

c) Synthesis of 4-allyloxy-1-hydroxybutyl-(1[3)-1,2-dideoxyglucose (3e)

20% strength trifluoroacetic acid (30 ml) is added to a solution of 2a (4.17 g, 14 mmol) in dichloromethane (340 ml). After 4 hours, toluene (200 ml) is added to this solution and it is concentrated to one half. Toluene is added to the mixture again and it is concentrated. The residue is chromatographed using dichloromethane/methanol (50:1[40:1 30:1). Compound 3e (3.26 g, 90%) is obtained.

$^1$H-NMR (300 MHz, CDCl$_3$): δ=1.53 (ddd, 1H, 2-H), 1.66 (m, 4H, CH$_2$CH$_2$), 2.0 (ddd, 1H, 2-H), 2.9 (bs, 1H, OH), 5.22 (m, 2H, O—CH$_2$—CH=CH$_2$), 5.9 (m, 1H, O—CH$_2$—CH=CH$_2$).

d) Synthesis of 4-phenyl-1-trifluoromethanesulfonyloxybutane (4e)

A mixture of 4-phenyl-1-butanol (3 ml, 20 mmol), pyridine (1.6 ml, 20 mmol) and dichloromethane (10 ml) is added dropwise with stirring to an ice-cold solution of trifluoromethanesulfonic anhydride (3.8 ml, 23 mmol) in dichloromethane (35 ml). After 1 hour, dichloromethane (65 ml) is added and the mixture is washed with water (3×20 ml), dried over magnesium sulfate and concentrated in vacuo at 25° C. The residue is chromatographed using hexane/ethyl acetate 7:1. Compound 4e (3.8 g, 70%) is obtained.

$^1$H-NMR (300 MHz, CDCl$_3$): δ=1.84 (m, 4, —CH$_2$—CH$_2$—), 2.67 (t, 2H, —CH$_2$-Ph), 4.52 (t, 2H, —CH$_2$-OTf), 7.24 (m, 5H, Ph).

e) Synthesis of 4-allyloxy-1-hydroxybutyl-(1[3)-[4-phenyl-1-hydroxybutyl-(1[6)-1,2-dideoxyglucose (5e)

A mixture of 3e (850 mg, 3.3 mmol), 4d (1.21 g, 4.3 mmol), potassium carbonate (684 mg, 4.95 mmol) and dibenzo-18-crown-6 (174 mg, 480 μmol) is stirred in toluene (14 ml) for 18 hours. For working-up, the mixture is filtered and chromatographed (toluene/acetone 10:1). Yield: (942 mg, 73%).

$^1$H-NMR (300 MHz, CDCl$_3$): δ=1.53 (ddd, 1H, 2-H), 1.66 (m, 8H, 4CH$_2$), 2.00 (m, 1H, 2-H), 2.60 (dd, 2H, CH$_2$Ph), 2.87 (bs, 1H, OH), 3.95 (m, 2H, O—CH$_2$—CH=CH$_2$), 5.22 (m, 2H, O—CH$_2$—CH=CH$_2$), 5.91 (m, 1H, O—CH$_2$—CH=CH$_2$).

f) Synthesis of 4-allyloxy-1-hydroxybutyl-(1[3)-[(2,3,4-tri-O-benzyl-α-L-fucopyranosyl)-(1[4)]-[4-phenyl-1-hydroxybutyl-(1[6)]-1,2-dideoxyglucose (6e)

The fucosylation is carried out as described in 3a.

g) Synthesis of 4-malonyl-1-hydroxybutyl-(1[3)-[(α-L-fucopyranosyl)-(1[4)]-[4-phenyl-1-hydroxy-butyl-(1[6)]-1,2-dideoxyglucose (7e)

Compound 7e is synthesized analogously to 7a (5 stages from 6e: deallylate, tosylate, malonylate, hydrogenate, hydrolyze).

$^1$H-NMR (300 MHz, D$_2$O): δ=1.0 (d, 3H, 6-H$_{fuc}$), 2.50 (t, 2H, Ch$_2$Ph), 2.90 (t, 2H), 4.20 (q, 1H, 5-H$_{fuc}$), 4.70 (d, 1H, 1-H$_{fuc}$).

It will be apparent to those skilled in the art that various modifications and variations can be made to the compositions and processes of this invention. Thus, it is intended that the present invention cover such modifications and variations, provided they come within the scope of the appended claims and their equivalents.

The disclosure of all publications cited above are expressly incorporated herein by reference in their entireties to the same extent as if each were incorporated by reference individually. The disclosure of German Patent Application Nos. P 44 08 248.7 (filed Mar. 11, 1994) for which benefit under 35 USC §119 is claimed, is expressly incorporated herein in its entirety.

What is claimed is:

1. A compound of formula I

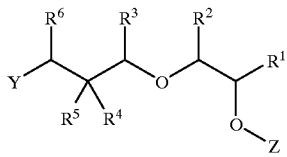

in which

R$^1$ and R$^2$ independently of one another are H, CH$_2$X or CH$_2$O(CH$_2$)$_m$X$^1$, wherein X and X$^1$ independently of one another are H, —NH$_2$, —COOH, —OH, —CH$_2$OH, —CH$_2$NH, —(CH$_2$)$_r$CH$_3$, aryl, —CH$_2$O(CH$_2$)$_q$H, —CH$_2$O(CH$_2$)$_q$NH$_2$, —CH$_2$O(CH$_2$)$_q$COOH, —CH$_2$O(CH$_2$)$_q$OH, —CH$_2$O(CH$_2$)$_q$CH$_2$OH, —CH$_2$O(CH$_2$)$_q$(CH$_2$)$_r$CH$_3$, or —CH$_2$O(CH$_2$)$_q$-Aryl, where r is 0 to 24, or R$^1$ and R$^2$ together form a six-membered carbo- or heterocycle which is either unsubstituted or has at least one substituent selected from the group consisting of R$^7$, R$^8$ and R$^9$, R$^3$ and R$^6$ together form a six-membered carbo- or heterocycle having at least one substituent X$^4$, R$^4$ and R$^5$ independently of one another are H, OH, CH$_2$OH, O(CR$^{10}$R$^{11}$)$_n$COOH, OCX$^3$$_2$(CR$^{10}$R$^{11}$)$_n$COOH, or OSO$_3$H, Y is O-α-NANA, O-β-NANA, or —O—CH$_2$—COOH, Z is a pyranose or a furanose, m, n, and q independently of one another are integers from 1 to 20, R$^7$, R$^8$, R$^9$, and X$^4$ independently of one another are —NH$_2$, —COOH, —CH$_2$OH, —CH$_2$NH, —(CH$_2$)$_r$CH$_3$, aryl, —CH$_2$O(CH$_2$)$_q$H, —CH$_2$O(CH$_2$)$_q$NH$_2$, —CH$_2$O(CH$_2$)$_q$COOH, —CH$_2$O(CH$_2$)$_q$OH, —CH$_2$O(CH$_2$)$_q$CH$_2$OH, —CH$_2$O(CH$_2$)$_q$(CH$_2$)$_r$CH$_3$, or —CH$_2$O(CH$_2$)$_q$-Aryl, where r is 0 to 24, X$^3$ is H, —(CH$_2$)$_r$CH$_3$, or aryl, or alternatively X$^3$$_2$ is =O or =S, and R$^{10}$ and R$^{11}$ independently of one another are X or —CH$_2$X or together form a six-membered carbo- or heterocycle having at least one substituent X$^4$, wherein said compound is other than the compounds sialyl-Lewis-X and -A and their derivatives, which derivatives, instead of an N-acetyl group, carry the substituents N$_3$, NH$_2$ or OH or which derivatives, instead of fucose, carry glycerol.

2. The compound of claim 1, wherein R$^1$ and R$^2$ independently are selected from the group consisting of H and —CH$_2$O(CH$_2$)$_5$CH$_3$, or R$^1$ and R$^2$ together form a six-membered carbocycle or a substituted tetrahydropyran ring, wherein R$^7$ and R$^8$ are H and R$^9$ is H or —CH$_2$O(CH$_2$)$_q$X.

3. The compound of claim 2, wherein R$^3$ and R$^6$ together form a β-D-galactosyl radical.

4. The compound of claim 2, wherein Z is an α-fucopyranosyl radical.

5. The compound of claim 2, wherein R$^3$ and R$^6$ together form a β-D-galactosyl radical and Z is an α-fucopyranosyl radical.

6. The compound of claim 5, wherein R$^1$ and R$^2$ independently are H or —CH$_2$—O—(CH$_2$)$_5$CH$_3$.

7. The compound of claim 5, wherein R$^1$ and R$^2$ together form a six-membered carbocycle.

8. The compound of claim 5, wherein R$^1$ and R$^2$ together form a substituted tetrahydropyran ring, wherein R$^7$ and R$^8$ are H and R$^9$ is H, CH$_2$OH, or —CH$_2$O(CH$_2$)$_q$X.

9. The compound of claim 8, wherein R$^9$ is —CH$_2$O(CH$_2$)$_q$X, q is 3 or 5 and X is H or aryl.

10. A compound of formula I

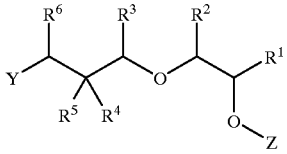

in which

R$^1$ and R$^2$ together form a six-membered carbo- or heterocycle which is either unsubstituted or has at least one substituent selected from the group consisting of R$^7$, R$^8$ and R$^9$, R$^3$ is =O, =S, H or —CH$_2$OX$^2$, R$^4$ and R$^5$ independently of one another are H, OH, CH$_2$OH, O(CR$^{10}$R$^{11}$)$_n$COOH, OCX$^3$$_2$(CR$^{10}$R$^{11}$)$_n$COOH, or OSO$_3$H, R$^6$ is H, —OH or —(CH$_2$)$_r$CH$_3$, or, with R$^3$, forms a six-membered carbo- or heterocycle having at least one substituent X$^4$, Y is O-α-NANA or O-β-NANA, Z is a pyranose or a furanose, m, n, and q independently of one another are integers from 1 to 20, and r is 0 to 24, R$^7$, R$^8$, R$^9$, and X$^4$ independently of one another are —NH$_2$, —COOH, —CH$_2$OH, —CH$_2$NH, —(CH$_2$)$_r$CH$_3$, aryl, —CH$_2$O(CH$_2$)$_q$H, —CH$_2$O(CH$_2$)$_q$NH$_2$, —CH$_2$O(CH$_2$)$_q$COOH, —CH$_2$O(CH$_2$)$_q$OH, —CH$_2$O(CH$_2$)$_q$CH$_2$OH, —CH$_2$O(CH$_2$)$_q$(CH$_2$)$_r$CH$_3$, or —CH$_2$O(CH$_2$)$_q$-Aryl, X$^3$ is H, —(CH$_2$)$_r$CH$_3$, or aryl or alternatively X$^3$$_2$ is =O or =S, R$^{10}$ and R$^{11}$ independently of one another are X or —CH$_2$X or together form a six-membered carbo- or heterocycle having at least one substituent X$^4$, wherein X and X$^2$ independently of one another are H, —NH$_2$, —COOH, —OH, —CH$_2$OH, —CH$_2$NH, —(CH$_2$)$_r$CH$_3$, aryl, —CH$_2$O(CH$_2$)$_q$H, —CH$_2$O(CH$_2$)$_q$NH$_2$, —CH$_2$O(CH$_2$)$_q$COOH, —CH$_2$O(CH$_2$)$_q$OH, —CH$_2$O(CH$_2$)$_q$CH$_2$OH, —CH$_2$O(CH$_2$)$_q$(CH$_2$)$_r$CH$_3$, or —CH$_2$O(CH$_2$O)$_q$-Aryl, wherein said compound is other than the compounds sialyl-Lewis-X and -A and their derivatives, which derivatives, instead of an N-acetyl group, carry the substituents $N_3$, $NH_2$ or OH or which derivatives, instead of fucose, carry glycerol.

11. The compound of claim 10, wherein $R^1$ and $R^2$ together form a six-membered carbocycle.

12. The compound of claim 11, wherein $R^7$, $R^8$, and $R^9$ are H.

13. The compound of claim 11, wherein $R^3$ and $R^6$ are H.

14. The compound of claim 11, where $R^3$ and $R^6$ together form a β-D-galactosyl radical.

15. The compound of claim 14, wherein said β-D-galactosyl radical is substituted in the 2-O-position by a hexyl group.

16. The compound of claim 11, wherein $R^4$ and $R^5$ independently are H, OH, or $CH_2OH$.

17. The compound of claim 11, wherein Z is an α-fucopyranosyl radical.

18. The compound of claim 11, wherein $R^7$, $R^8$, and $R^9$ are H, $R^3$ and $R^6$ are H, and Z is an α-fucopyranosyl radical.

19. The compound of claim 18, wherein $R^4$ and $R^5$ independently are H, OH, or $CH_2OH$.

20. A compound of formula I

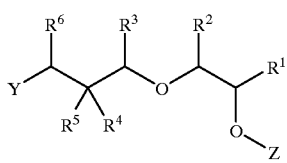

in which
$R^1$ and $R^2$ independently of one another together form a six-membered carbo- or heterocycle which is either unsubstituted or has at least one substituent selected from the group consisting of $R^7$, $R^8$ and $R^9$,
$R^3$ and $R^6$ together form a six-membered carbo- or hetero-cycle having at least one substituent $X^4$,
$R^4$ and $R^5$ independently of one another are H, OH, $O(CR^{10}R^{11})_n COOH$, $OCX^3_2(CR^{10}R^{11})_n COOH$, or $OSO_3H$,
Y is O-α-NANA or O-β-NANA,
Z is a pyranose, a furanose or an open-chain polyalcohol,
m, n, and q independently of one another are integers from 1 to 20,
$R^7$, $R^8$, $R^9$, and $X^4$ independently of one another are $-NH_2$, $-COOH$, $-CH_2OH$, $-CH_2NH$, $-(CH_2)_r CH_3$, aryl, $-CH_2O(CH_2)_q H$, $-CH_2O(CH_2)_q NH_2$, $-CH_2O(CH_2)_q COOH$, $-CH_2O(CH_2)_q OH$, $-CH_2O(CH_2)_q CH_2OH$, $-CH_2O(CH_2)_q C_1-C_{25}$-Alkyl, or $-CH_2O(CH_2)_q$-Aryl, where r is 0 to 24,
$X^3$ is H, $-(CH_2)_r CH_3$, or aryl or alternatively
$X^3_2$ is =O or =S and
$R^{10}$ and $R^{11}$ independently of one another are X or $-CH_2X$ or together form a six-membered carbo- or heterocycle having at least one substituent $X^4$,
X is H, $-NH_2$, $-COOH$, $-OH$, $-CH_2OH$, $-CH_2NH$, $-(CH_2)_r CH_3$, aryl, $-CH_2O(CH_2)_q H$, $-CH_2O(CH_2)_q NH_2$, $-CH_2O(CH_2)_q COOH$, $-CH_2O(CH_2)_q OH$, $-CH_2O(CH_2)_q CH_2OH$, $-CH_2O(CH_2)_q C_1-C_{25}$-Alkyl, or $-CH_2O(CH_2)_q$-Aryl, where r is 0 to 24,
wherein said compound is other than the compounds sialyl-Lewis-X and -A and their derivatives, which derivatives, instead of an N-acetyl group, carry the substituents $N_3$, $NH_2$ or OH or which derivatives, instead of fucose, carry glycerol.

21. The compound of claim 20, wherein Z is a pyranose or $-CH_2C(CH_2OH)_3$.

22. The compound of claim 21, wherein said pyranose is selected from the group consisting of α-fucopyranosyl radical, an α-mannosyl radical, and an α-glucosyl radical.

23. The compound of claim of claim 20, wherein $R^1$ and $R^2$ together form a six-membered carbocycle and $R^7$, $R^8$ and $R^9$ are H.

24. The compound of claim 23, wherein $R^3$ and $R^6$ together form a β-D-galactosyl radical.

25. The compound of claim 24, wherein Z is an α-fucopyranosyl radical.

26. The compound of claim 24, wherein Z is an α-mannosyl radical.

27. The compound of claim 24, wherein Z is an α-glucosyl radical.

28. The compound of claim 21, wherein Z is $-CH_2C(CH_2OH)_3$.

29. A pharmaceutical composition comprising a compound according to claim 1 in a pharmaceutically acceptable carrier.

30. A pharmaceutical composition comprising a compound according to claim 10 in a pharmaceutically acceptable carrier.

31. A pharmaceutical composition comprising a compound according to claim 20 in a pharmaceutically acceptable carrier.

32. A method of inhibiting the binding of a selectin to a carbohydrate ligand on a cell expressing said carbohydrate ligand, comprising the step of administering to a subject a therapeutically effective dose of the pharmaceutical composition of claim 1.

33. A method of inhibiting the binding of a selectin to a carbohydrate ligand on a cell expressing said carbohydrate ligand, comprising the step of administering to a subject a therapeutically effective dose of the pharmaceutical composition of claim 10.

34. A method of inhibiting the binding of a selectin to a carbohydrate ligand on a cell expressing said carbohydrate ligand, comprising the step of administering to a subject a therapeutically effective dose of the pharmaceutical composition of claim 20.

35. A method of inhibiting selectin-mediated cell adhesion, comprising administering to a subject a therapeutically effective dose of the pharmaceutical composition of claim 1.

36. A method of inhibiting selectin-mediated cell adhesion, comprising administering to a subject a therapeutically effective dose of the pharmaceutical composition of claim 10.

37. A method of inhibiting selectin-mediated cell adhesion, comprising administering to a subject a therapeutically effective dose of the pharmaceutical composition of claim 20.

38. A compound of formula I

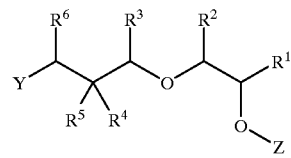

in which
$R^1$ and $R^2$ independently of one another are H, $CH_2X$ or $CH_2O(CH_2)_m X^1$, wherein X and $X^1$ independently of one another are H, $-NH_2$, $-COOH$, $-OH$, —$CH_2OH$, —$CH_2NH$, —$(CH_2)_rCH_3$, aryl or —$CH_2O(CH_2)_qH$, —$CH_2O(CH_2)_qNH_2$, —$CH_2O(CH_2)_qCOOH$, —$CH_2O(CH_2)_qOH$, —$CH_2O(CH_2)_qCH_2OH$, —$CH_2O(CH_2)_q(CH_2)_rCH_3$, or —$CH_2O(CH_2)_q$-Aryl, where r is 0 to 24, or together form a six-membered carbocycle which is either unsubstituted or has at least one substituent selected from the group consisting of $R^7$, $R^8$ and $R^9$, $R^3$ and $R^6$ together form a six-membered carbo- or heterocycle having at least one substituent $X^4$, $R^4$ and $R^5$ independently of one another are H, OH, $CH_2OH$, $O(CR^{10}R^{11})_nCOOH$, $OCX^3{}_2(CR^{10}R^{11})_nCOOH$, or $OSO_3H$, Y is O-α-NANA, O-β-NANA, or —O—$CH_2$—COOH, Z is a pyranose or a furanose, m, n, and q independently of one another are integers from 1 to 20, $R^7$, $R^8$, $R^9$, and $X^4$ independently of one another are —$NH_2$, —COOH, —$CH_2OH$, —$CH_2NH$, —$(CH_2)_rCH_3$, aryl, —$CH_2O(CH_2)_qH$, —$CH_2O(CH_2)_qNH_2$, —$CH_2O(CH_2)_qCOOH$, —$CH_2O(CH_2)_qOH$, —$CH_2O(CH_2)_qCH_2OH$, —$CH_2O(CH_2)_q(CH_2)_rCH_3$, or —$CH_2O(CH_2)_q$-Aryl, where r is 0 to 24, $X^3$ is —$(CH_2)_rCH_3$, or aryl, or alternatively $X^3{}_2$ is =O or =S, and $R^{10}$ and $R^{11}$ independently of one another are X or —$CH_2X$ or together form a six-membered carbo- or heterocycle having at least one substituent $X^4$, wherein said compound is other than the compounds sialyl-Lewis-X and -A and their derivatives, which derivatives, instead of an N-acetyl group, carry the substituents $N_3$, $NH_2$ or OH or which derivatives, instead of fucose, carry glycerol.

\* \* \* \* \*